(12) United States Patent
Davison et al.

(10) Patent No.: US 11,613,740 B2
(45) Date of Patent: Mar. 28, 2023

(54) PLUG FOR OIL FIELD SERVICE WORK AND METHOD OF PRODUCTION

(71) Applicant: Tally Production Systems, LLC, Houston, TX (US)

(72) Inventors: Douglas Wayne Davison, Tomball, TX (US); Shane Davison, Tomball, TX (US)

(73) Assignee: Tally Production Systems, LLC, Houston, TX (US)

( * ) Notice: Subject to any disclaimer, the term of this patent is extended or adjusted under 35 U.S.C. 154(b) by 0 days.

(21) Appl. No.: 16/825,422

(22) Filed: Mar. 20, 2020

(65) Prior Publication Data

US 2020/0300058 A1    Sep. 24, 2020

Related U.S. Application Data

(60) Provisional application No. 62/821,649, filed on Mar. 21, 2019.

(51) Int. Cl.
| | |
|---|---|
| *E21B 33/129* | (2006.01) |
| *C12N 9/16* | (2006.01) |
| *A23K 20/189* | (2016.01) |
| *C12N 15/81* | (2006.01) |
| *E21B 43/26* | (2006.01) |

(52) U.S. Cl.
CPC .............. *C12N 9/16* (2013.01); *A23K 20/189* (2016.05); *C12N 15/81* (2013.01); *C12Y 301/03008* (2013.01); *E21B 33/1293* (2013.01); *E21B 43/26* (2013.01)

(58) Field of Classification Search
CPC .................................................... E21B 33/1293
See application file for complete search history.

(56) References Cited

U.S. PATENT DOCUMENTS

| | | | | |
|---|---|---|---|---|
| 4,444,252 | A  * | 4/1984 | Fisher, Jr. ........... | E21B 33/1295 166/134 |
| 8,408,290 | B2 * | 4/2013 | Porter ................. | E21B 33/1277 166/134 |
| 2007/0119600 | A1* | 5/2007 | Slup ..................... | E21B 33/134 166/387 |
| 2009/0011247 | A1* | 1/2009 | Barlow ................ | F16L 55/1108 428/413 |
| 2014/0166317 | A1* | 6/2014 | Gregory .............. | E21B 33/1204 166/387 |
| 2017/0268310 | A1* | 9/2017 | Shkurti ................ | E21B 33/134 |
| 2020/0347694 | A1* | 11/2020 | Power ..................... | E21B 23/06 |

* cited by examiner

*Primary Examiner* — Taras P Bemko
*Assistant Examiner* — Ronald R Runyan
(74) *Attorney, Agent, or Firm* — Park, Vaughan, Fleming & Dowler LLP

(57) ABSTRACT

Plugs for use in hydrocarbon recovery operations having lower and upper anchor slip assemblies with individual anchors, upper and lower elements, a shoe and tubular mandrel.

10 Claims, 25 Drawing Sheets

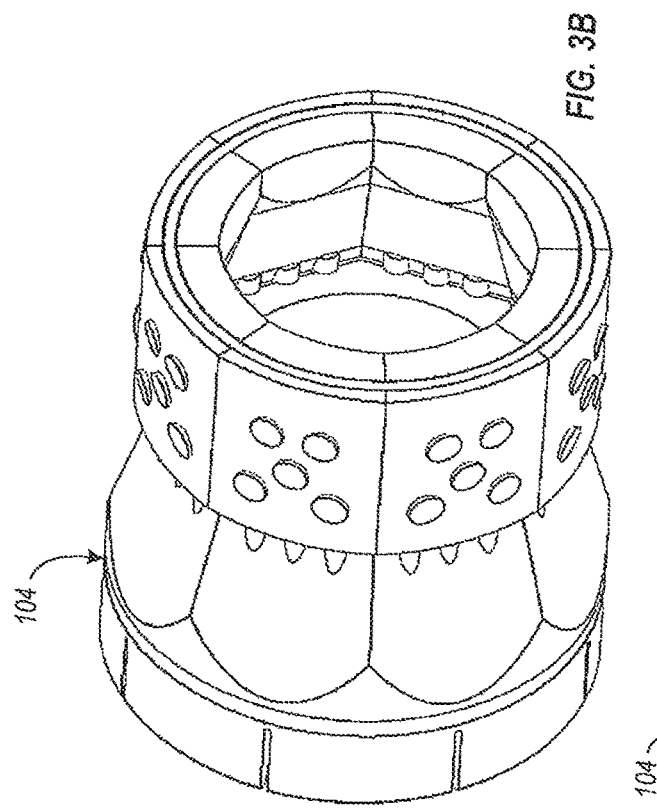
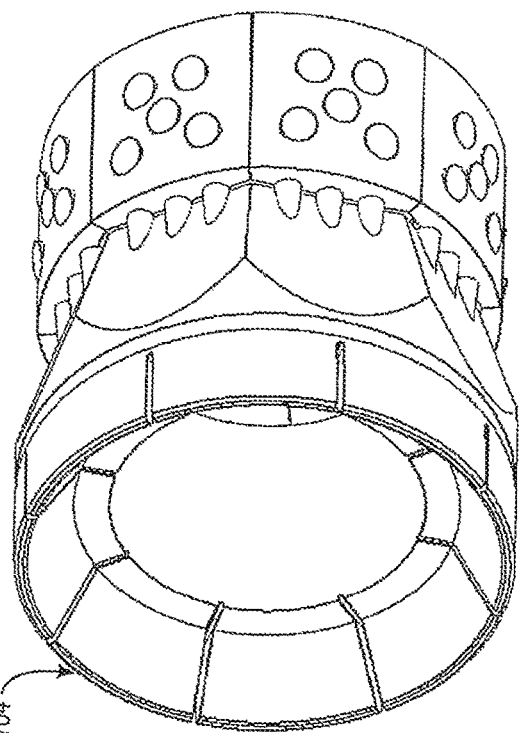
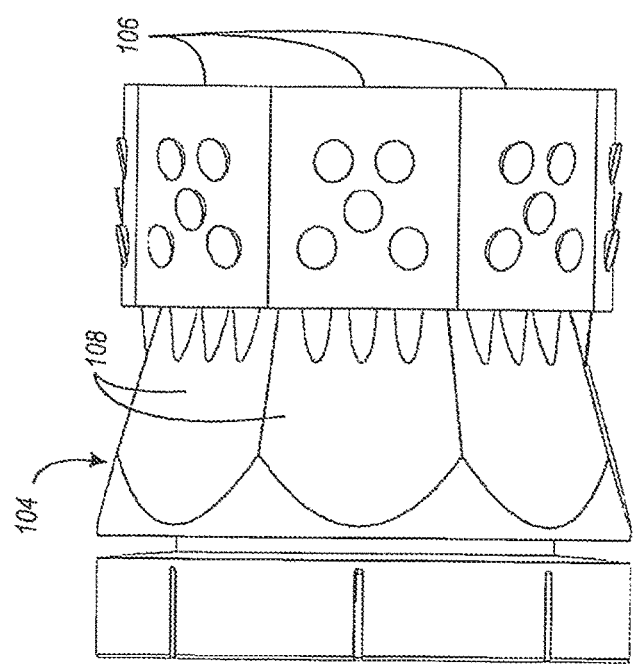
FIG. 3A
FIG. 3B
FIG. 3C

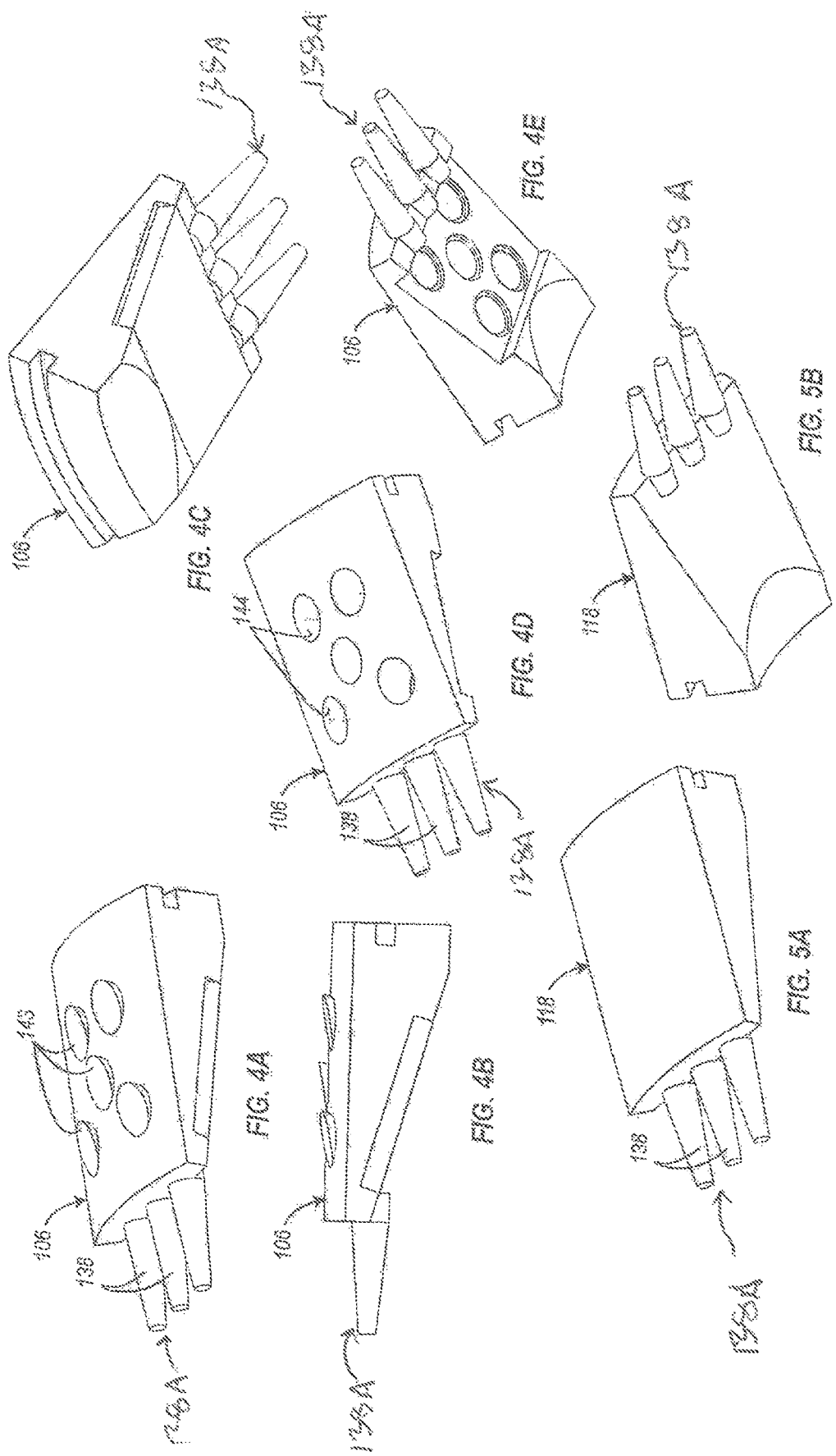

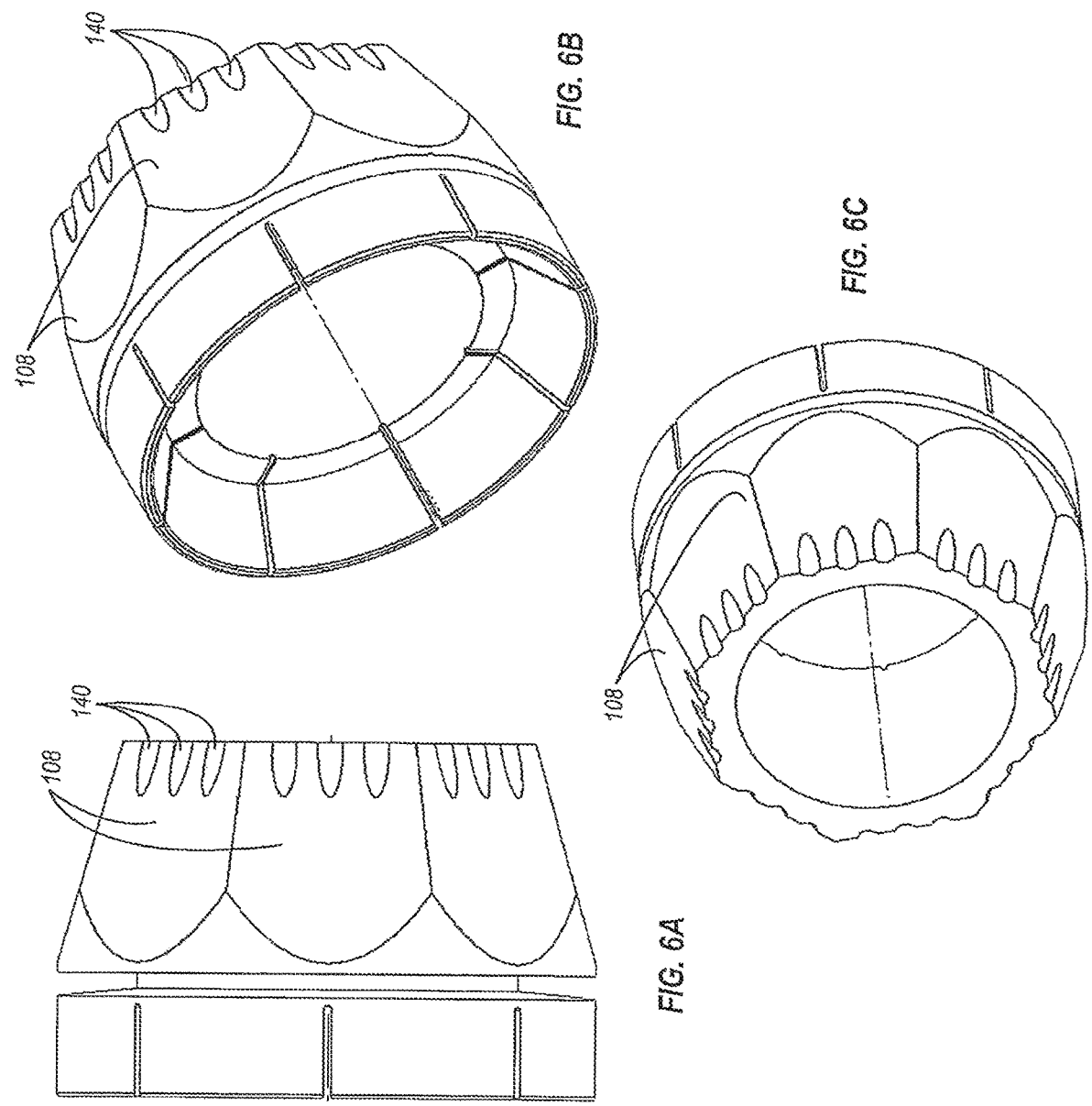

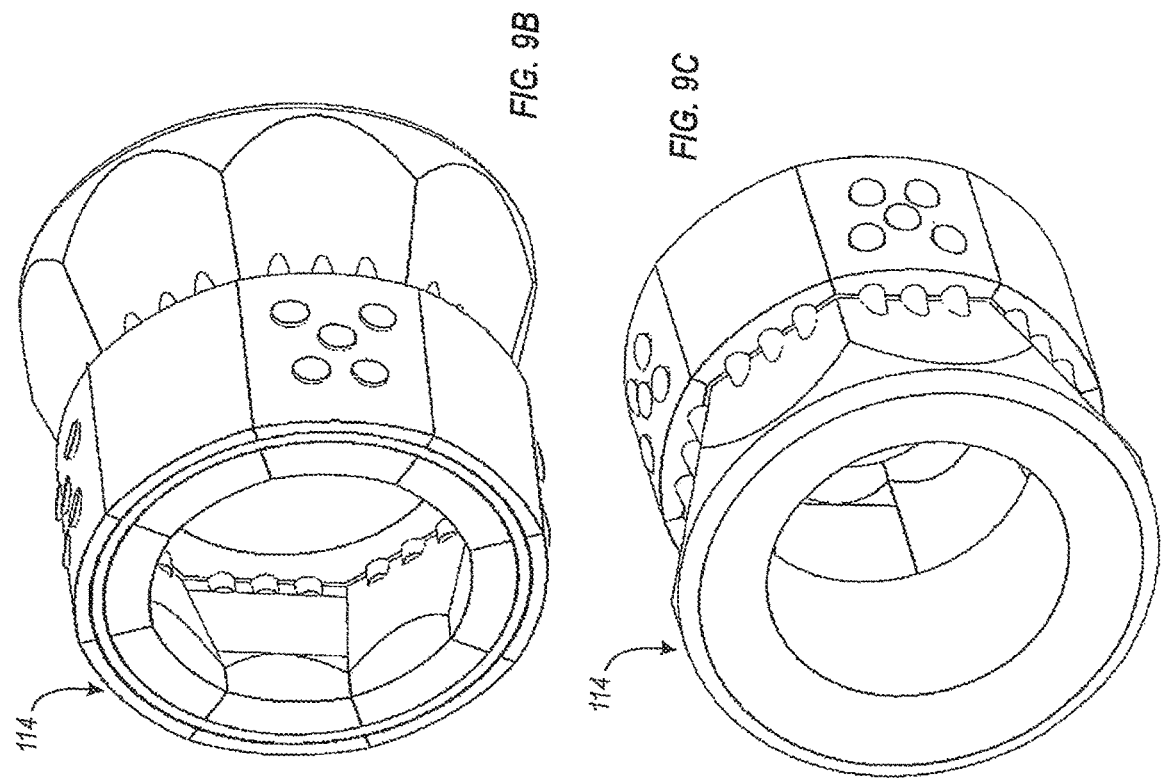
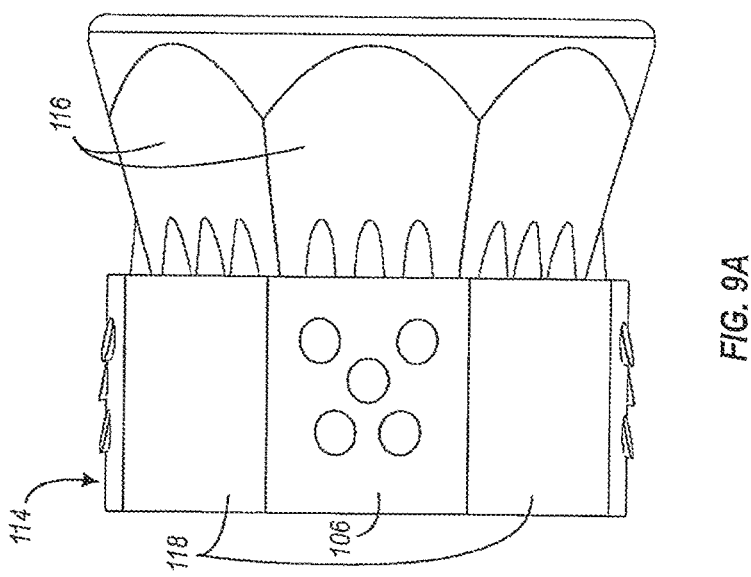

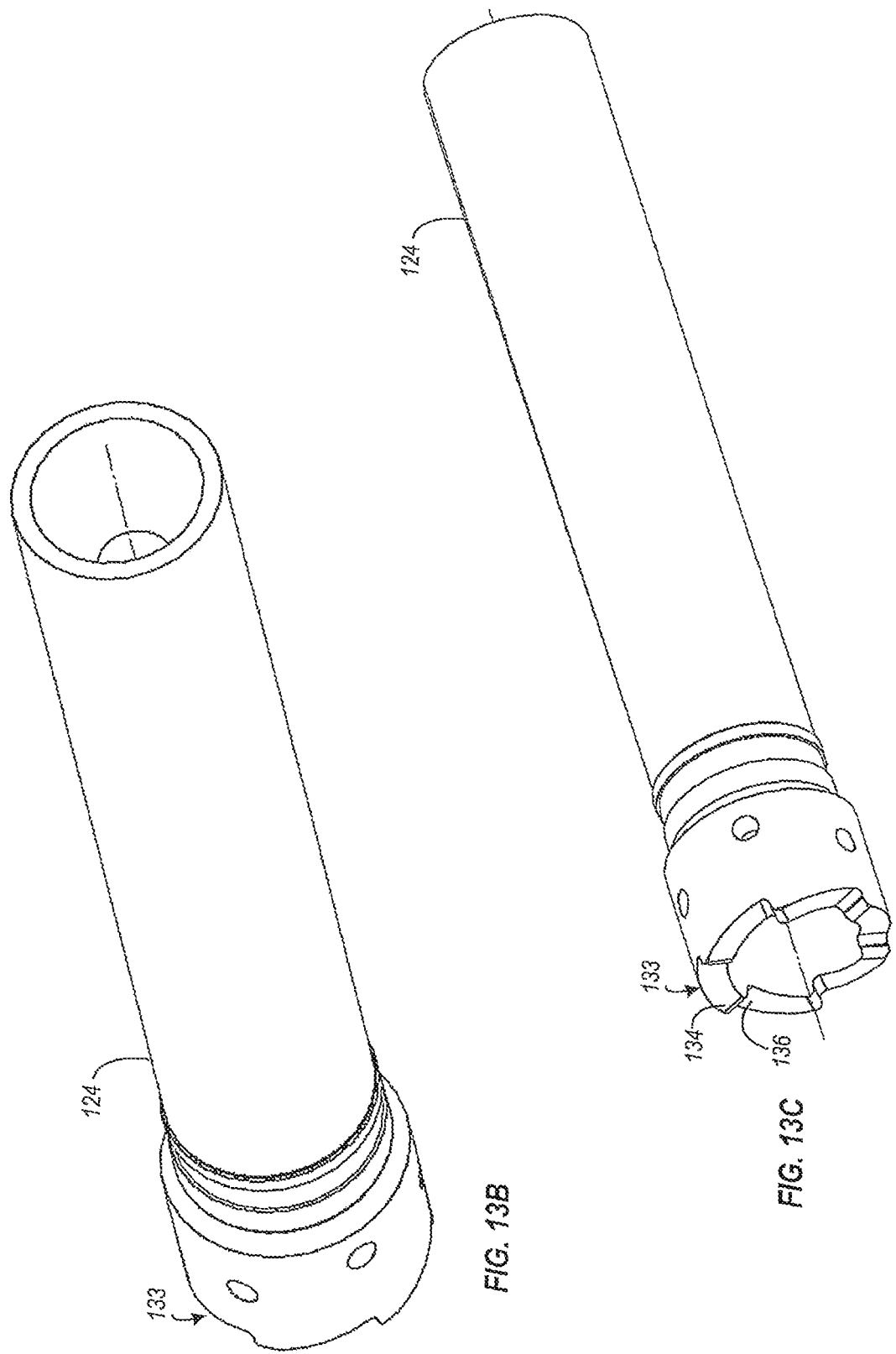

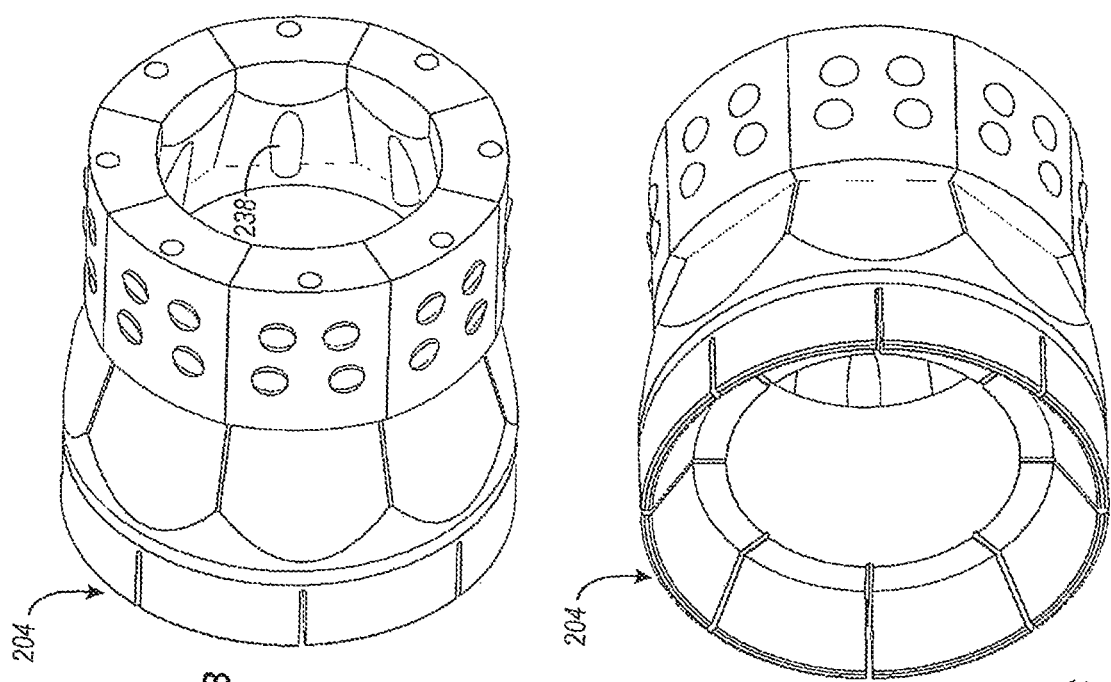
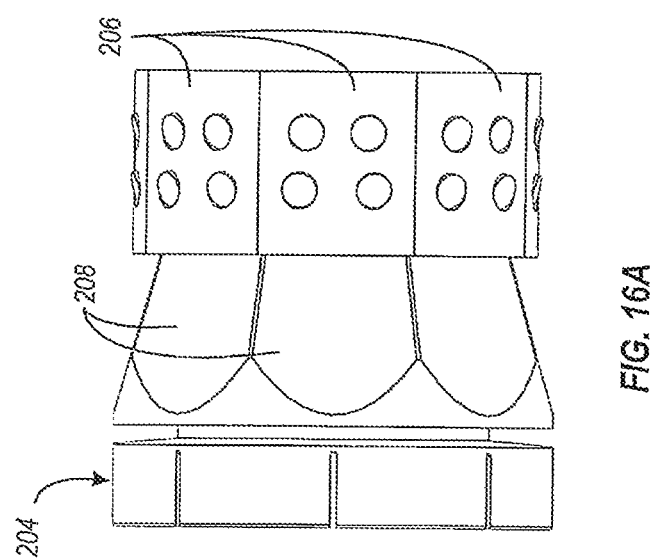

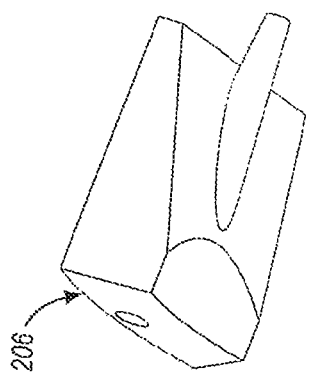
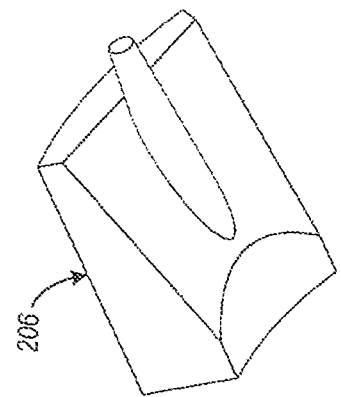
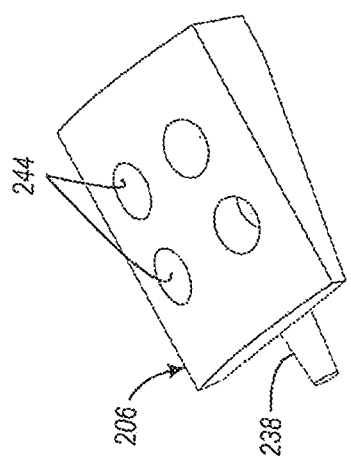
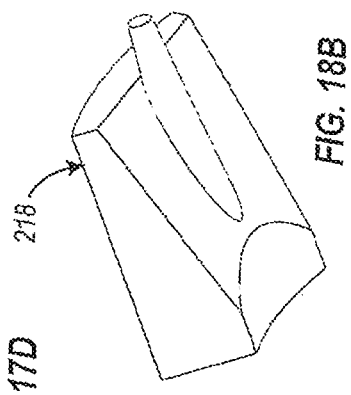
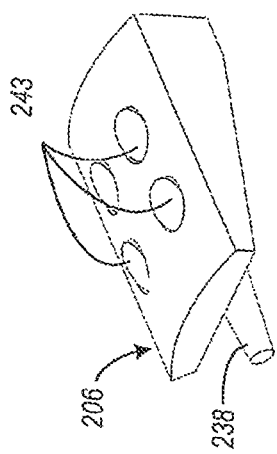
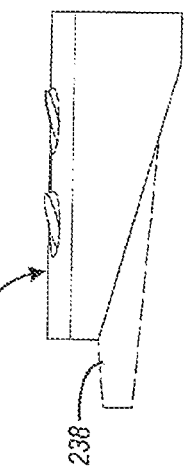

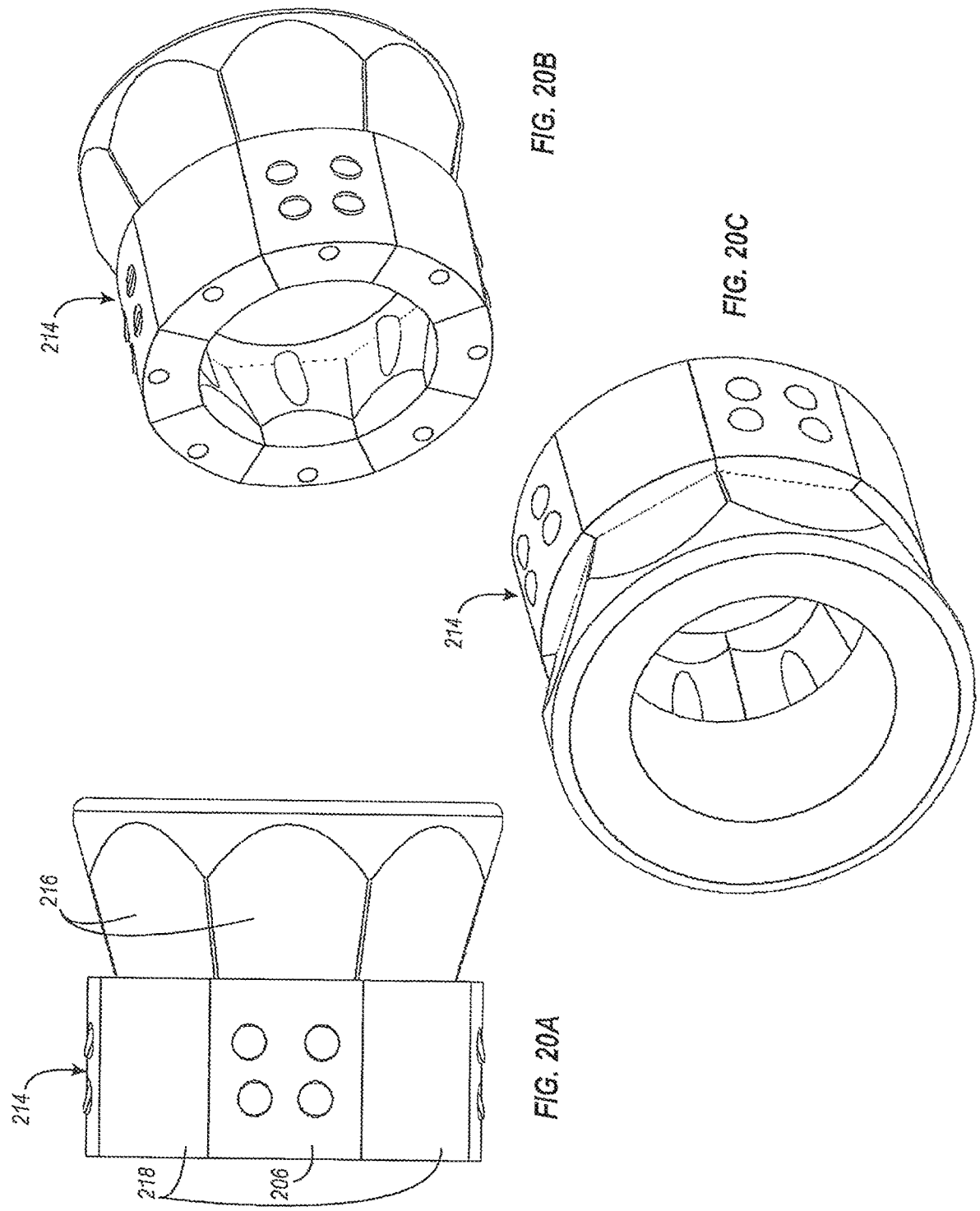

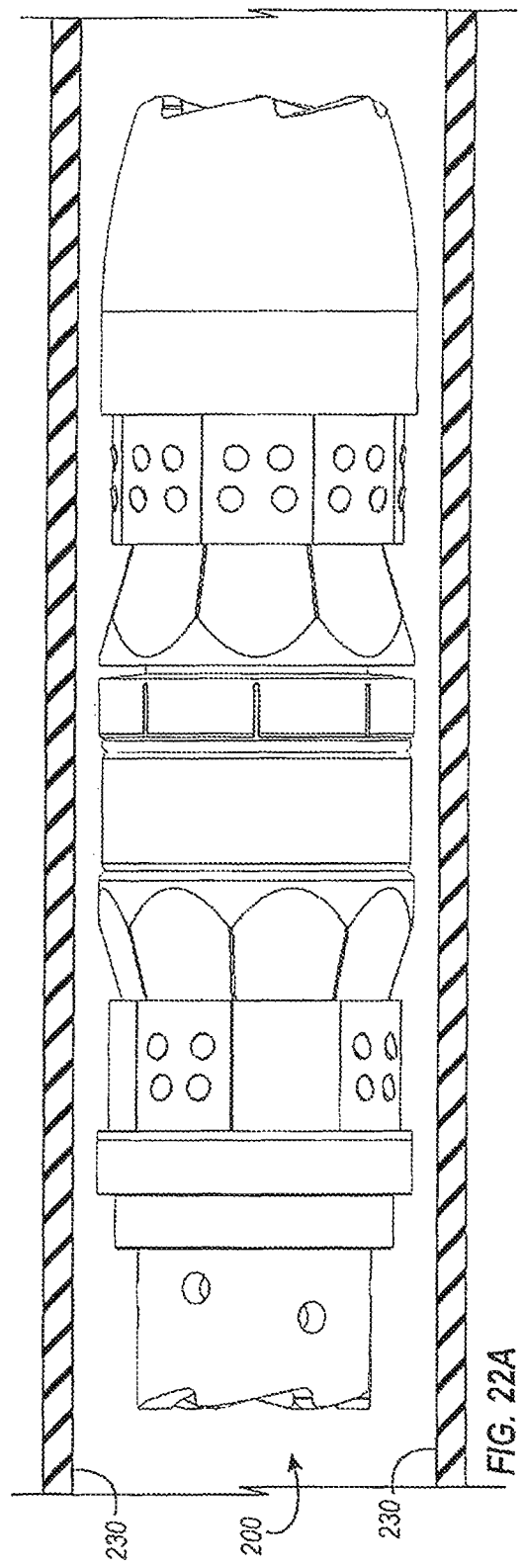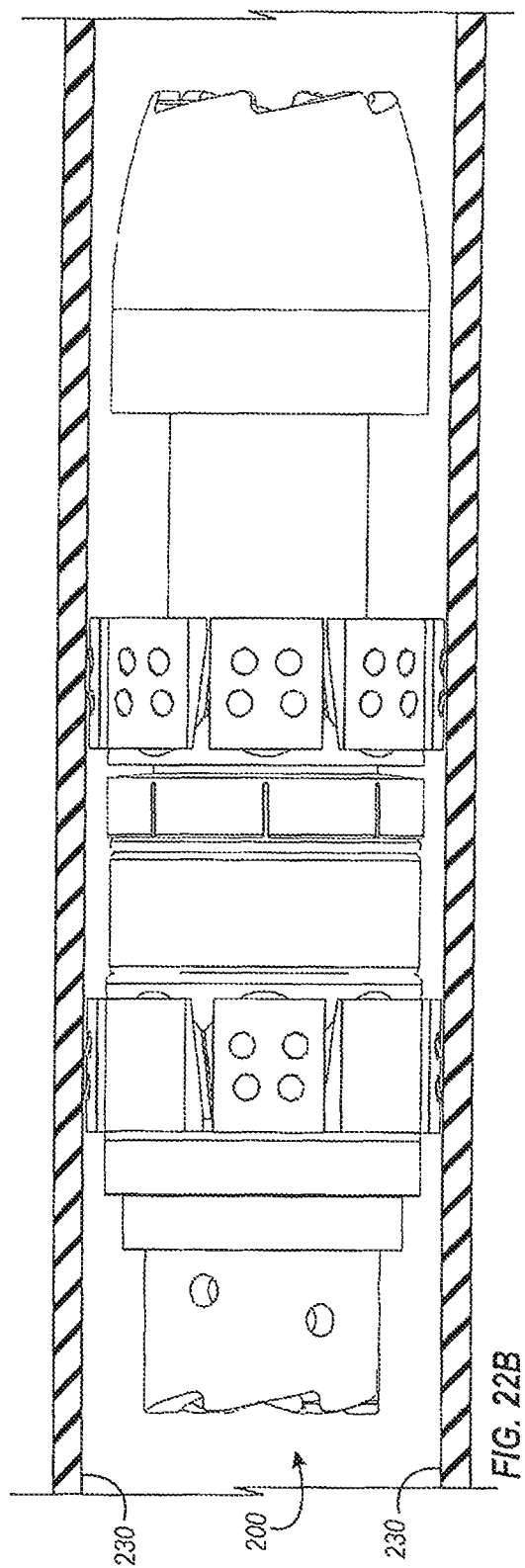

PLUG FOR OIL FIELD SERVICE WORK AND METHOD OF PRODUCTION

CROSS-REFERENCE TO RELATED APPLICATIONS

The present application claims priority to U.S. Provisional Application 62/821,849 filed Mar. 21, 2019, the entirety of which is incorporated by reference.

FIELD OF THE INVENTION

This disclosure relates to plugs. In particular, this disclosure is drawn to plugs that are used in hydrocarbon recovery applications, such as frac plugs, bridge plugs, as well as cement retainers, wherein these units have unique features that improve performance and decrease cost.

BACKGROUND OF THE INVENTION

In oil and gas well completion operations, plugs are used for zonal isolation and multi-zone hydraulic fracturing processes. Generally, frac plugs are devices that are used to selectively isolate sections of a well and are used either alone or in combination with other frac plugs and other downhole tools. Oil and gas wells drilled into the ground generally define a well bore that extends (horizontally and/or vertically) for some length underground. Sections of a well bore are typically lined with a well bore casing. During a fracking process, fluids are injected into ground formations through perforations in the well bore casing. By isolating sections of a well, frac plugs permit well operators to inject fluids into selected perforations in different zones of the well. These isolated sections may be fractured, thereby permitting hydrocarbons to flow into the developed fractures.

SUMMARY

In one example embodiment, a plug is described. The plug may comprise a shoe, a lower anchor slip assembly having a first end and a second end, the lower anchor slip assembly connected at the first end to the shoe, the lower anchor slip assembly having a number of independent anchors to expand from a first diameter size to a second diameter size, a lower element connected to the second end of the lower anchor slip assembly and an upper element connected to the lower element. The plug may also comprise an upper anchor slip assembly having an upper anchor slip assembly first end and an upper anchor slop assembly second end, the upper anchor slip assembly connected to the upper element first end, the upper anchor slip assembly having a number of independent anchors to expand from a first diameter size to a second diameter size; a load ring connected to the upper anchor slip assembly second end, and a load ring wedge connected to the load ring. The plug may also comprise a tubular mandrel placed at least partially within the shoe, the lower anchor slip assembly, the lower element, the upper element, the upper anchor slip assembly, the load ring and the load ring wedge, wherein linear movement of the tubular mandrel causes movement of the upper anchor slip assembly to expand a set of upper anchor slips in a radial direction and linear movement of the tubular mandrel is further configured to expand a set of lower anchor slips in a radial direction.

In another example embodiment, a plug is described. The plug may comprise a shoe configured with a lower clutch mechanism, a lower anchor slip assembly having a first end and a second end, the lower anchor slip assembly positioned at the first end to the shoe, the lower anchor slip assembly having a number of independent anchors to expand from the first diameter size to the second diameter size the lower slip assembly configured to expand from a first diameter size to a second diameter size and a lower element positioned next to the second end of the lower anchor slip assembly. The plug may further comprise an upper element connected to the lower element, and an upper anchor slip assembly having an upper anchor slip assembly first end and an upper anchor slip assembly second end, the upper anchor slip assembly having a number of independent upper anchors to expand from the first upper anchor slip assembly diameter size to the second upper anchor slip assembly diameter size, the upper anchor slip assembly positioned next to the upper element first end, the upper anchor slip assembly configured to expand from a first upper anchor slip assembly diameter size to a second upper anchor slip assembly diameter size. The plug may further comprise a load ring positioned next to the upper anchor slip assembly second end; a load ring wedge connected to the load ring and a tubular mandrel placed at least partially within the shoe, the lower anchor slip assembly, the lower element, the upper element, the upper anchor slip assembly, the load ring and the load ring wedge, wherein linear movement of the tubular mandrel causes movement of the upper anchor slip assembly to expand a set of upper anchor slips in a radial direction and linear movement of the tubular mandrel is further configured to expand a set of lower anchor slips in a radial direction.

In another example embodiment, a method of making a plug is disclosed comprising producing each of a shoe, a lower anchor slip assembly, a lower element, an upper element, an upper anchor slip assembly with individually positionable anchors, a load ring and a tubular mandrel, wherein each of the shoe, the lower anchor slip assembly with individually postionable anchors, the lower element, the upper element, the upper anchor slip assembly, the load ring and the tubular mandrel are configured in a heated assembly arrangement and wherein no machining is required. The method may also comprise assembling the plug wherein the plug has the lower anchor slip assembly having a first end and a second end, the lower anchor slip assembly connected at the first end to the shoe, a lower element connected to the second end of the lower anchor slip assembly, an upper element connected to the lower element, an upper anchor slip assembly having an upper anchor slip assembly first end and an upper anchor slip assembly second end, the upper anchor slip assembly connected to the upper element first end, the upper anchor slip assembly having a number of independent anchors to expand from a first diameter size to a second diameter size. The method may also provide for the load ring connected to the upper anchor slip assembly second end, the load ring wedge connected to the load ring and the tubular mandrel placed at least partially within the shoe, the lower anchor slip assembly, the lower element, the upper element, the upper anchor slip assembly, the load ring and the load ring wedge, wherein linear movement of the tubular mandrel causes movement of the upper anchor slip assembly to expand a set of upper anchor slips in a radial direction and linear movement of the tubular mandrel is further configured to expand a set of lower anchor slips in a radial direction.

BRIEF DESCRIPTION OF THE DRAWINGS

Aspects of the present disclosure are illustrated by way of example and not as a limitation in the figures of the accompanying drawings, in which like references indicate similar elements and in which:

FIGS. 3A-3C are side and isometric views of the lower anchor slip assembly shown in FIG. 1.

FIGS. 4A-4E are side and isometric views of one of the anchor slips shown in FIG. 1.

FIGS. 5A-5B are side and isometric views of one of the blank anchor slips shown in FIG. 1.

FIGS. 6A-6C are side and isometric views of the a lower wedge shown in FIG. 1.

FIGS. 9A-9C are side and isometric views of the upper anchor slip assembly shown in FIG. 1.

FIGS. 13A-13E are side, end, and isometric views of the mandrel shown in FIG. 1.

FIGS. 16A-16C are side and isometric views of the lower anchor slip assembly shown in FIG. 15.

FIGS. 17A-17E are side and isometric views of one of the anchor slips shown in FIG. 15.

FIGS. 18A-18B are side and isometric views of one of the anchor slips shown in FIG. 15.

FIGS. 20A-20C are side and isometric views of the upper anchor slip assembly shown in FIG. 15.

FIGS. 22A-22B are side views of the frac plug shown in FIG. 15 inside a well bore casing in un-set and set configurations.

DETAILED DESCRIPTION

Aspects of the present disclosure relate to plugs and retainers used in hydrocarbon recovery operations. As a non-limiting example, frac plugs may be used with hydraulic fracturing ("fracking") processes for zonal isolation and multi zone fracking processes. Generally, hydraulic fracturing is a well stimulation technique in which rock is fractured by a pressurized liquid. The process involves the high-pressure injection of fracking fluid into a well bore to create cracks in the rock formations through which hydrocarbons will flow more freely.

During a typical fracking process, a frac plug is set by a setting tool and the well bore casing is perforated for a distance above the frac plug. A frac ball (e.g., a ball made of fiberglass or other suitable material) is placed against a ball seat of the frac plug to act as a check valve to seal the section(s) below the frac plug. Next, the perforated section is fractured by pressurized fracking fluid. After this, another frac plug is set above the first perforated section to isolate the section(s) below the new frac plug. This process repeats, as necessary. A typical hydrocarbon well may have 30-60 sections, depending on various factors. Described below is a novel frac plug that solves various problems found in the prior art.

Figure 1A:
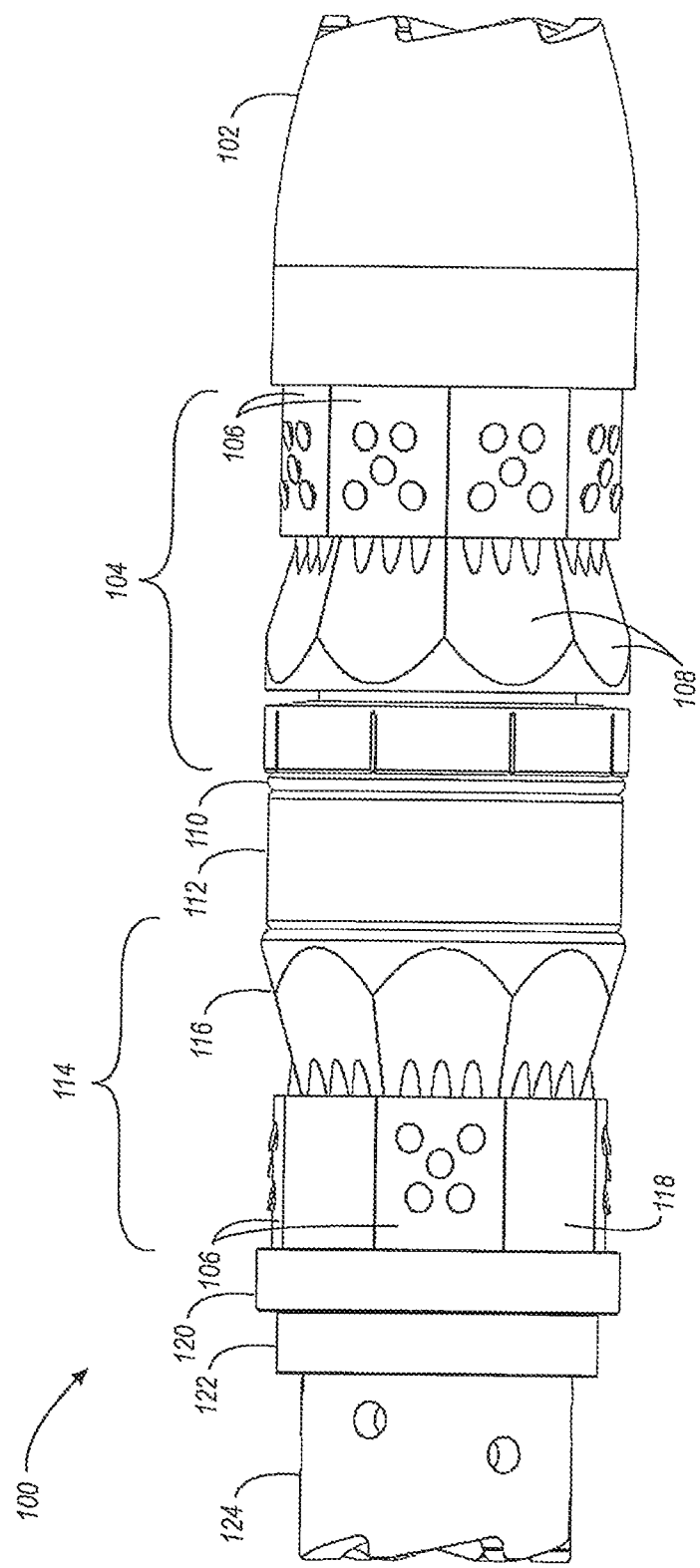
FIGS. 1A-1C are side and isometric views of a frac plug assembly.
Figure 1B:
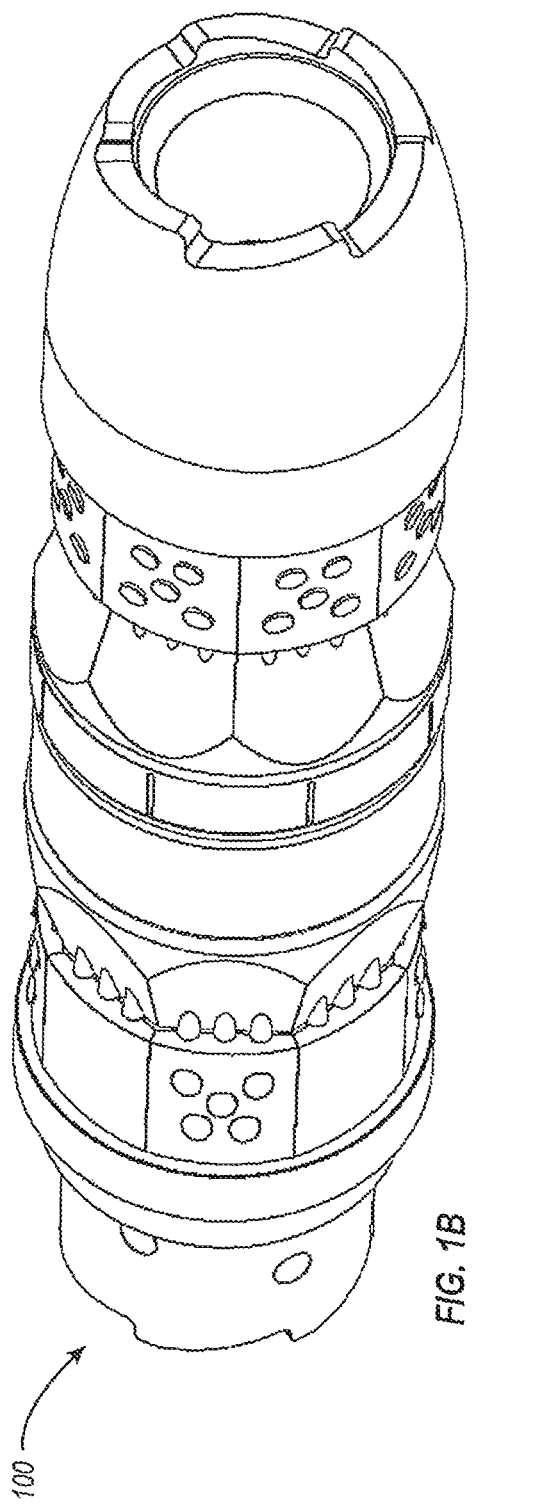
Figure 1C:
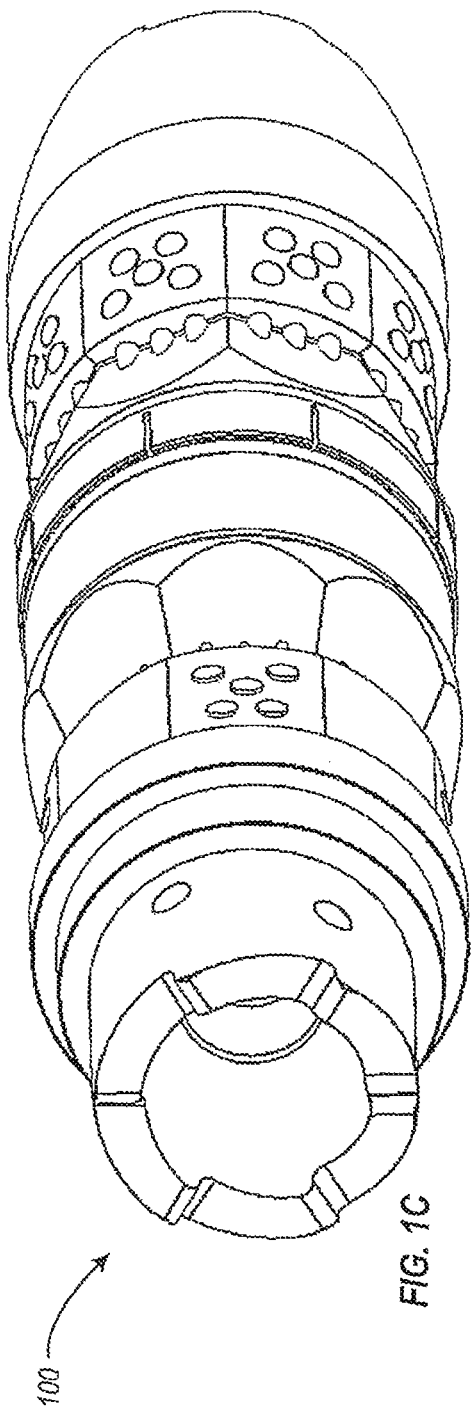

FIGS. 1A-1C are side and isometric views of a frac plug assembly. Although the description is for a frac plug type assembly, other types of plugs or retainers may use a similar or identical construction. In the following description, the terms "upper" and "lower" are intended to indicate a relative position with respect to a well bore, where "upper" is toward the opening of a well bore (e.g., at the surface) and "lower" is toward the end of the well bore. Similarly, the terms "above" and "below" are intended to indicate a relative position with respect to the opening of a well bore, where "above" means closer to the opening or surface. At the lower end of frac plug 100 is a shoe 102. The shoe 102 is described in more detail below with respect to FIGS. 2A-2B. Above the shoe 102 is a lower anchor slip assembly 104. The lower anchor slip assembly 104 further comprises anchor slips 106 and lower wedge 108. The lower anchor slip assembly 104 is described in more detail below with respect to FIGS. 3A-3C. The anchor slips 106 are described in more detail below with respect to FIGS. 4A-4E. The lower wedge 108 is described in more detail below with respect to FIGS. 6A-6C.

Above the lower anchor slip assembly 104 is a lower element 110. The lower element 110 is described in more detail below with respect to FIGS. 7A-7B. Above the lower element 110 is upper element 112. The upper element 112 is described in more detail below with respect to FIGS. 8A-8B. Above the upper element 112 is upper anchor slip assembly 114. The upper anchor slip assembly 114 is described in more detail below with respect to FIGS. 9A-9C. The upper anchor slip assembly 114 further comprises anchor slips 106, anchor slips 118, and upper wedges 116. The anchor slips 106 and 118 are described in more detail below with respect to FIGS. 4A-4E and 5A-5B. The upper wedge 116 is described in more detail below with respect to FIGS. 10A-10C.

Above the upper anchor slip assembly 114 is load ring 120 and load ring wedge 122. The load ring 120 and load ring wedge 122 are described in more detail below with respect to FIGS. 11A-11B and 12A-12B. FIGS. 1A-1C also show tubular mandrel 124, which extends along most of the length of the frac plug 100. The tubular mandrel 124 is described in more detail below with respect to FIGS. 13A-13E.

Figure 2B:
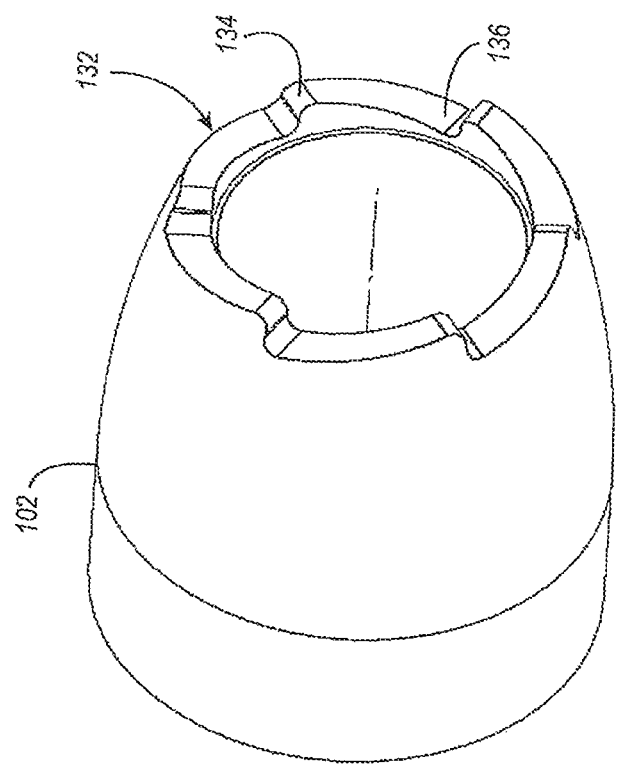
FIGS. 2A-2B are isometric views of the shoe shown in FIG. 1.
Figure 2A:
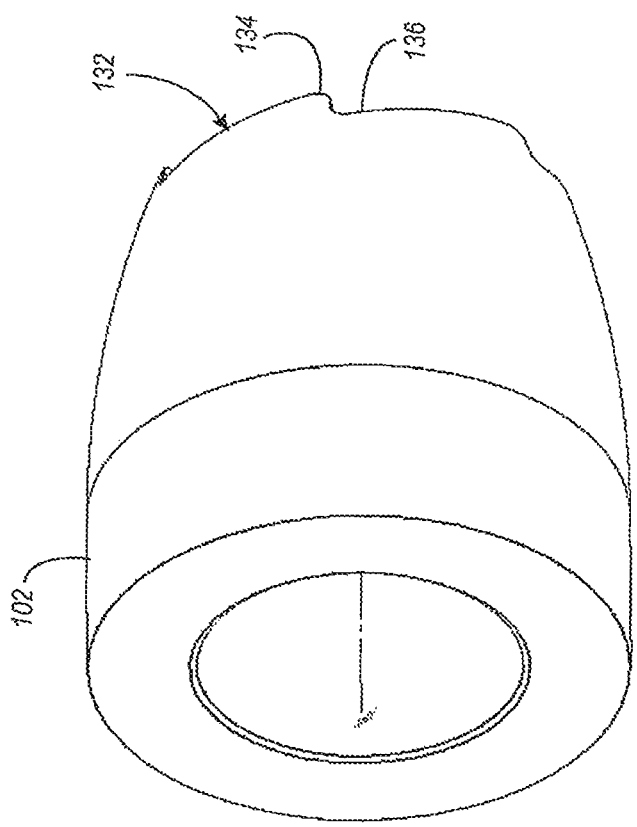

FIGS. 2A-2B are isometric views of the shoe 102 shown in FIG. 1. As shown in FIG. 1, the shoe 102 is located at the lower/front end of the frac plug assembly 100. A lower clutching mechanism 132 is formed at the lower end of the shoe 102. The clutching mechanism 132 includes a series of protrusions 134 and valleys 136 that are configured to mate with, opposite protrusions 134 and valleys 136 on the upper end of the mandrel 124 (described below with respect to FIGS. 13A-13E and 14A-14C). When the lower clutch mechanism 132 of the shoe 102 engages the clutching mechanism 133 of a mandrel 124 on a previously set frac plug 100, the combination of the lower clutch mechanism 132 and the clutching mechanism 133 of the mandrel 124 allows for engagement of a previously set frac plug 100 wherein at least one of the protrusions 134 can engage a mating surface of the previously set frac plug 100. (described below with respect to FIGS. 14A-14C). In these embodiments all clutch mechanisms allow for a self-centering capability around the 360 degrees of the tool. Since there are multiple surfaces for interface, there are multiple locking positions. Such combinations of previously set frac plugs 100 with the lower clutch mechanism 132 allows for a centralizing of the shoe 102 on to the frac plug 100. As will be discussed with FIG. 23, an anchor plate 2300 may be used in connection with embodiments described.

FIGS. 3A-3C are side and isometric views of the lower anchor slip assembly 104 shown in FIG. 1. The lower anchor slip assembly 104 includes eight anchor slips 106 which each engage a corresponding lower wedge 108. As shown best in FIGS. 4A-4E, each anchor slip 106 has three anchors 138 extending toward the corresponding lower wedge 108. FIGS. 6A-6C are side and isometric views of the lower wedge 108 shown in FIG. 1. Each lower wedge 108 has three grooves 140 that are configured to receive an anchor 138 of a corresponding anchor slip 106. The combination of anchors 138 and grooves 140 help keep the anchor slips 106 aligned as they move relative to the wedge 108 when a frac plug 100 is set (described below with respect to FIGS. 22A-22B). Each anchor slip 106 includes one or more metal ceramic composite (MCC) buttons 143 that extend outward from the anchor slip 106. In the example shown in FIG. 4, each anchor slip 106 has five buttons 143. Other examples are also possible, as one skilled in the art would understand, therefore the use of metal ceramic composite buttons 143 should not be considered limiting. For example, embodiments of the disclose may allow for some anchors 138 to use metal ceramic composite buttons, while others use a ceramic button. For example, in one example embodiment, anchors buttons at the top of the configuration may use a ceramic composition, while metal ceramic buttons may be used at the lower or bottom buttons. FIG. 4D shows the anchor slip 106 without buttons 143. As shown, for each button 143, a corresponding hole 144 is formed to receive a button 143. When a frac plug 100 is set (described below), the buttons 143 engage the inner surface of the well bore casing or pipe, locking the frac plug 100 in place. As illustrated, each of the anchors 138 may be composed of a set of fingers 138A.

Figure 8B:
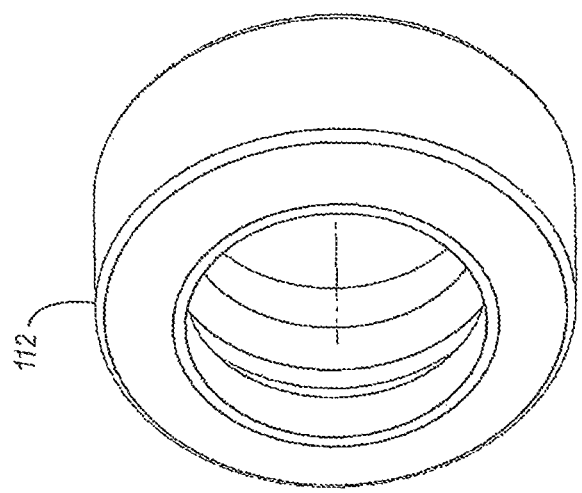
FIGS. 8A-8B are side and isometric views of the upper element shown in FIG. 1.
Figure 8A:
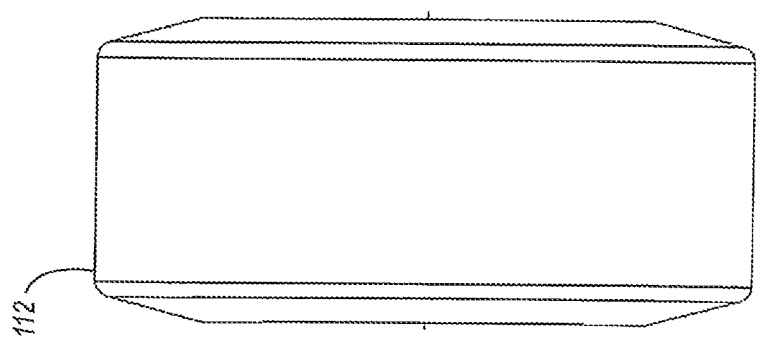
Figure 7B:
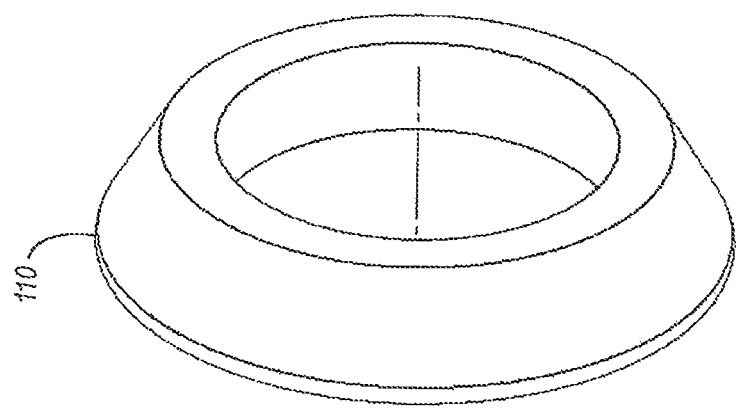
FIGS. 7A-7B are side and isometric views of the lower element shown in FIG. 1.
Figure 7A:
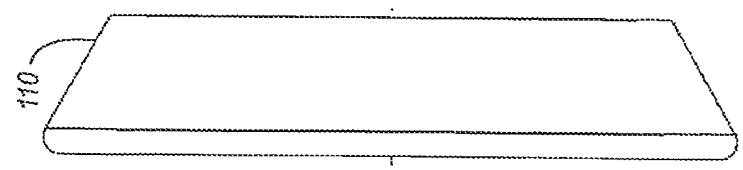

FIGS. 7A-7B are side and isometric views of the lower element 110 shown in FIG. 1. The lower element 110 is a rubber sealing element. FIGS. 8A-8B are side and isometric views of the upper element 112 shown in FIG. 1.

FIGS. 9A-9C are side and isometric views of the upper anchor slip assembly 114 shown in FIG. 1. The upper anchor slip assembly 114 is similar to the lower anchor slip assembly 104. The upper anchor slip assembly 114 includes eight anchor slips 106. In this example, four of the anchor slips 106 are the same as those on the lower anchor slip assembly 104. The other four anchor slips are blank anchor slips 118 that do not have MCC buttons 143. FIGS. 5A-5B are isometric views of a blank anchor slip 118. The number of buttons 143 used can be selected by a designer based on various factors. For example, it is typically desired to have as little metal as possible in a well bore, so a user may select the minimum number of buttons 143 that will adequately lock the frac plug 100 when it is set.

Figure 10C:
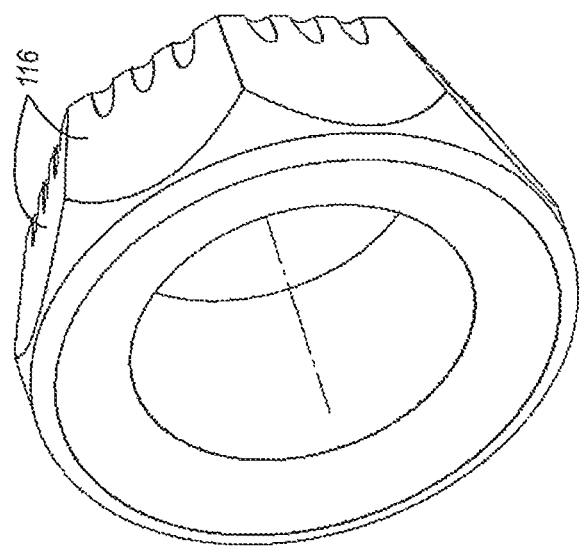
FIGS. 10A-10C are side and isometric views of the an upper wedge shown in FIG. 1.
Figure 10B:
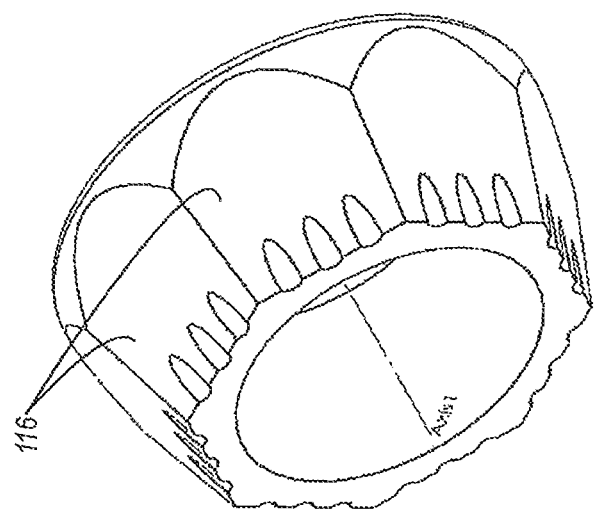
Figure 10A:
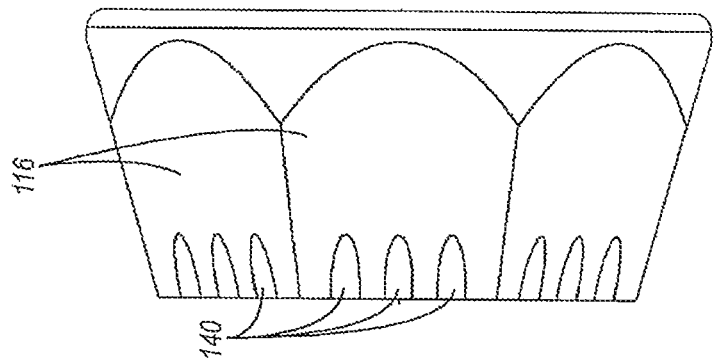

As shown in FIGS. 4A-4E and 5A-5B, each anchor slip 106 and 118 has three anchors 138 extending toward the corresponding upper wedge 116. FIGS. 10A-10C are side and isometric views of the upper wedge 116 shown in FIG. 1. Each upper wedge 116 has three grooves 140 that are configured to receive an anchor 138 of a corresponding anchor slip 106 or 118. The combination of anchors 138 and grooves 140 help keep the anchor slips 106 and 118 aligned as they move relative to the wedge 116 when a frac plug 100 is set (described below with respect to FIGS. 22A-22B).

Figure 11B:
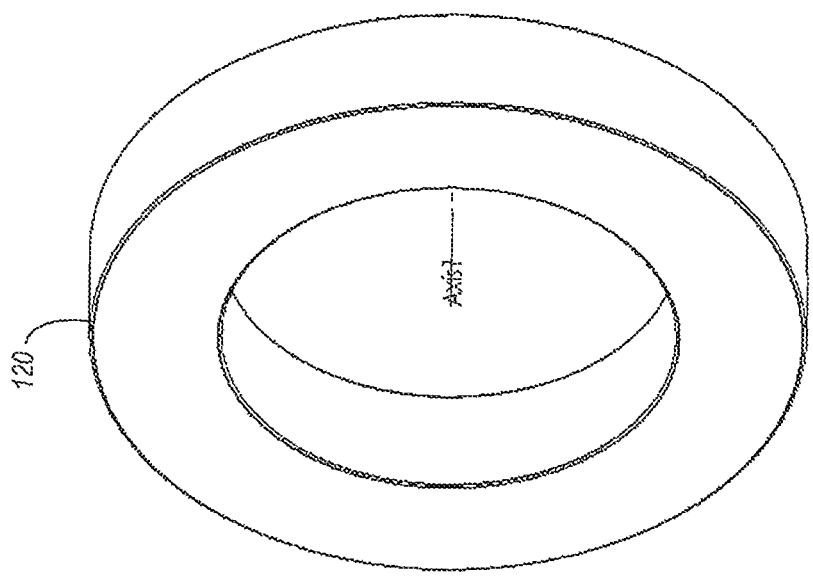
FIGS. 11A-11B are side and isometric views of the load ring shown in FIG. 1.
Figure 11A:
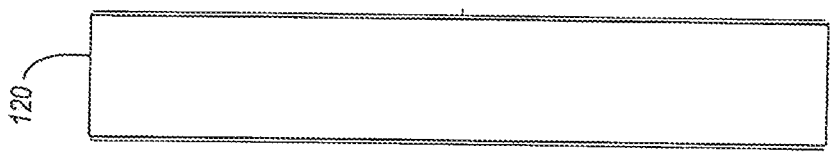
Figure 12C:
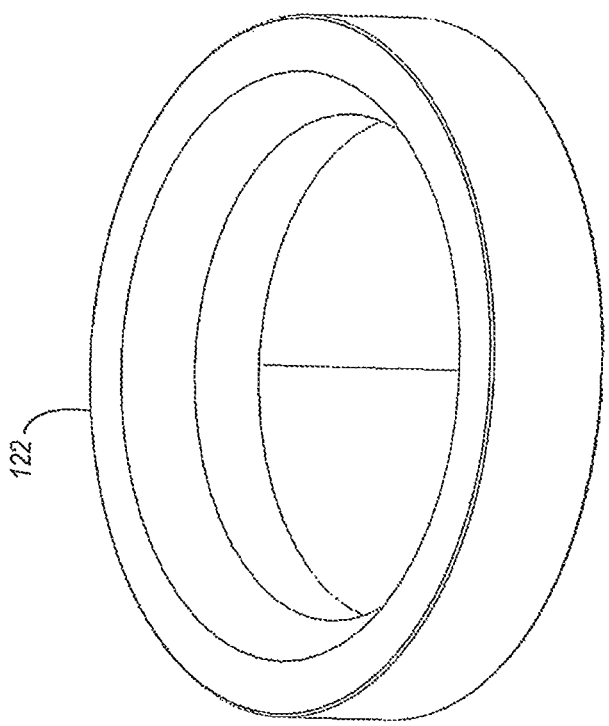
FIGS. 12A-12C are side and isometric views of the load ring wedge shown in FIG. 1.
Figure 12B:
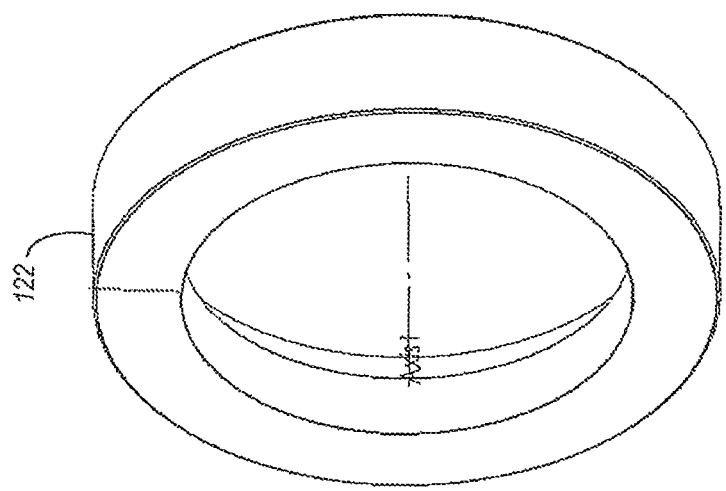
Figure 12A:
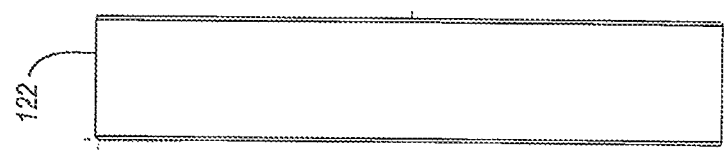
Figure 13A:
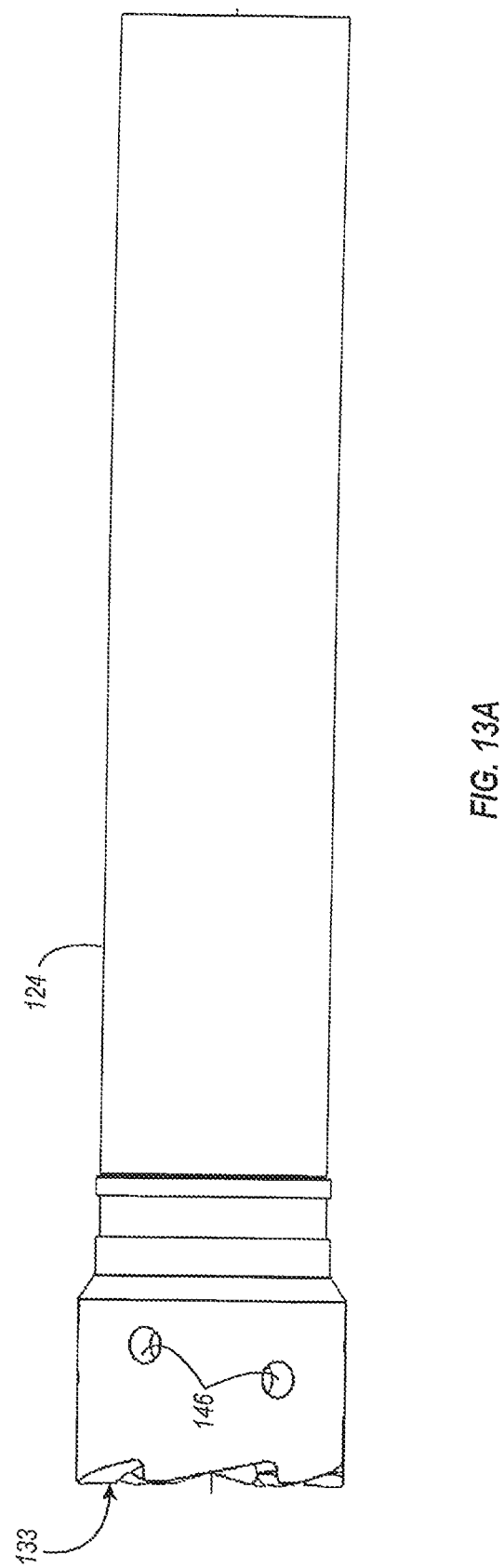
Figure 13E:
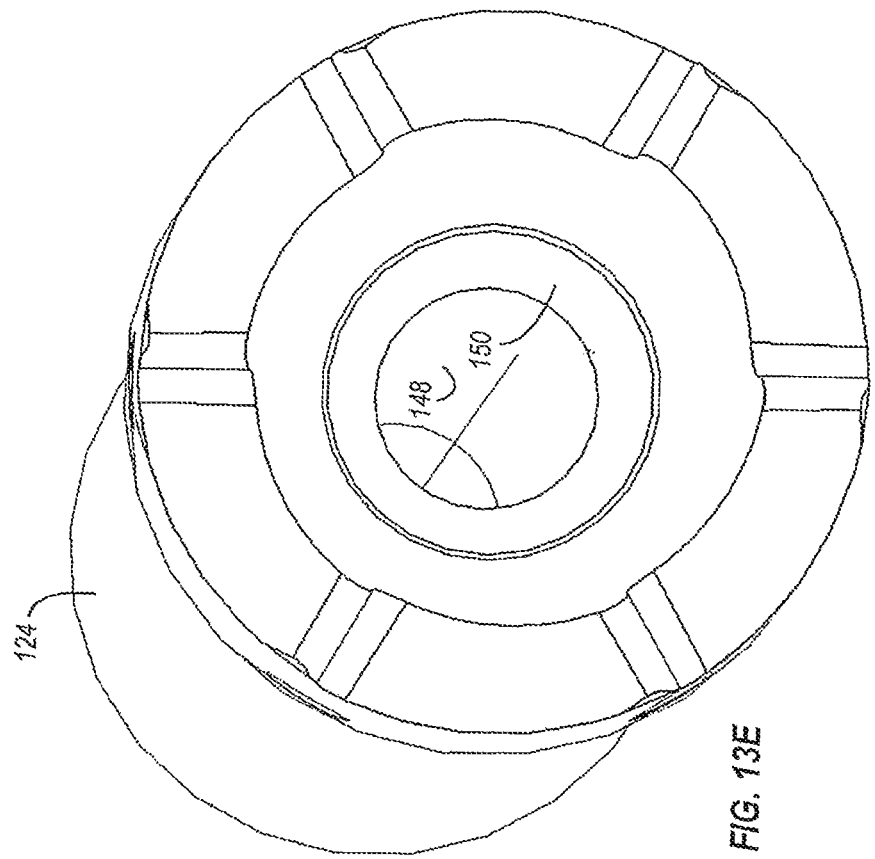
Figure 13D:
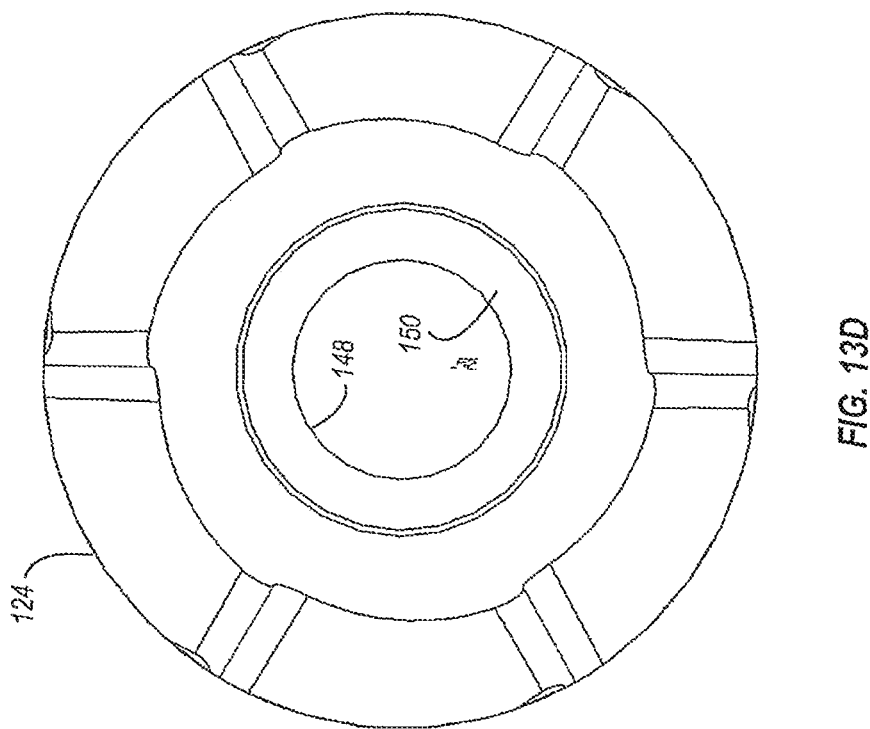

FIGS. 11A-11B are side and isometric views of the load ring 120 shown in FIG. 1. FIGS. 12A-12C are side and isometric views of the load ring wedge 122 shown in FIG. 1. When setting the frac plug 100, the setting tool will engage the load ring 120 to set the frac plug 100 (described below).

FIGS. 13A-13E are side, end, and isometric views of the mandrel 124 shown in FIG. 1. The mandrel 124 is generally tubular with a hollow center that forms a passageway 148 (FIG. 13D-13E) that allows fluid to flow through the frac plug 100 before being sealed by seating a frac ball against the seat 150 of the mandrel 124 (described below). An upper clutching mechanism 133 is formed at the upper end of the mandrel 124. The clutching mechanism 133 includes a series of protrusions 134 and valleys 136 that are configured to mate with opposite protrusions and valleys on the lower end of the shoe 122 of another frac plug 100. A plurality of holes 146 are formed near the upper end of the mandrel 124 for attaching a setting tool using shear screws, as one skilled in the art would understand. At the upper end of the mandrel 124, a seat 150 (FIG. 13D-13E) is formed for receiving a frac ball for sealing the well bore when the frac plug 100 is set.

The mandrel 124 described above can be manufactured in any desired manner, as one skilled in the art would understand. Typically, mandrels are manufactured by starting with a tubing material, and machining/turning the desired shape, including machining the inner passageway. While this manufacturing process works, it can be time consuming and expensive. In one example, the mandrel 124 described above can be manufactured with a fiberglass reinforced plastic using a filament winding process. The filament winding process results in a precisely formed inner diameter, without the disadvantages of a machining process.

Figure 14A:
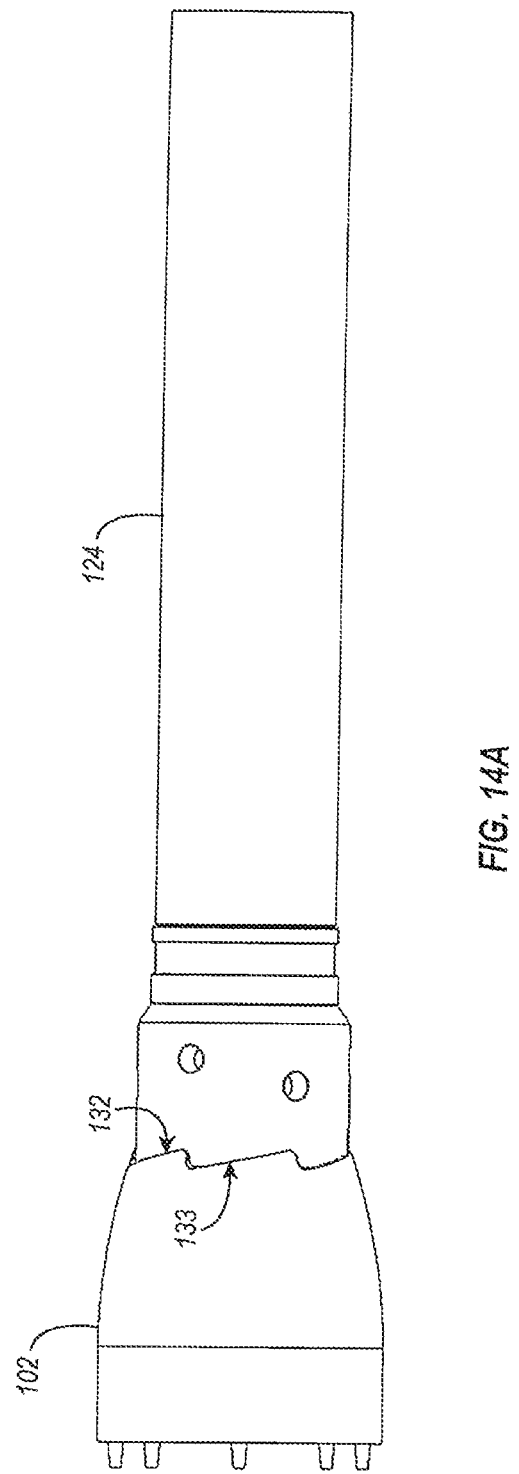
FIGS. 14A-14C are side and isometric views depicting a mating shoe and mandrel like those depicted in FIG. 1.
Figure 14B:
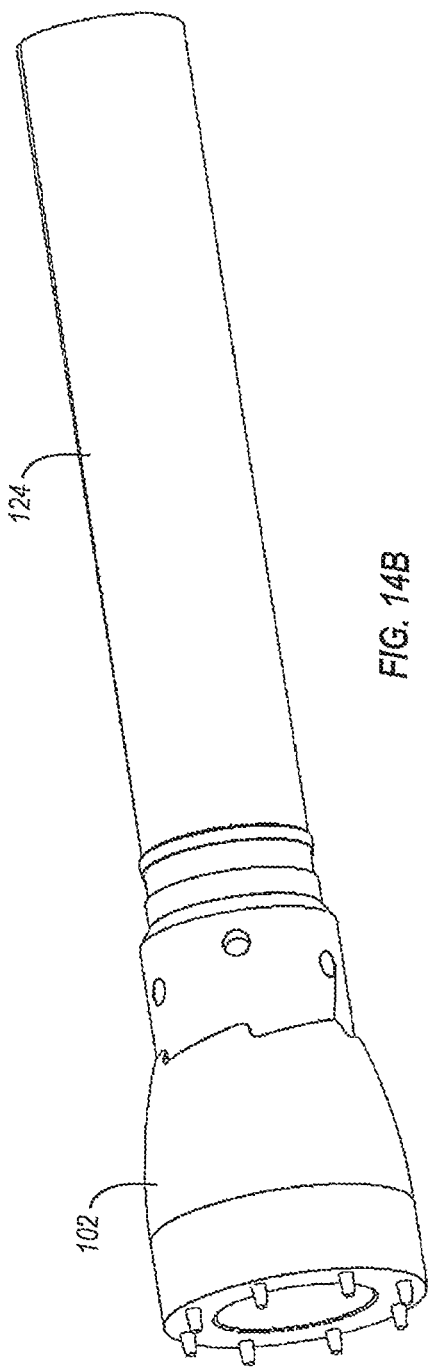
Figure 14C:
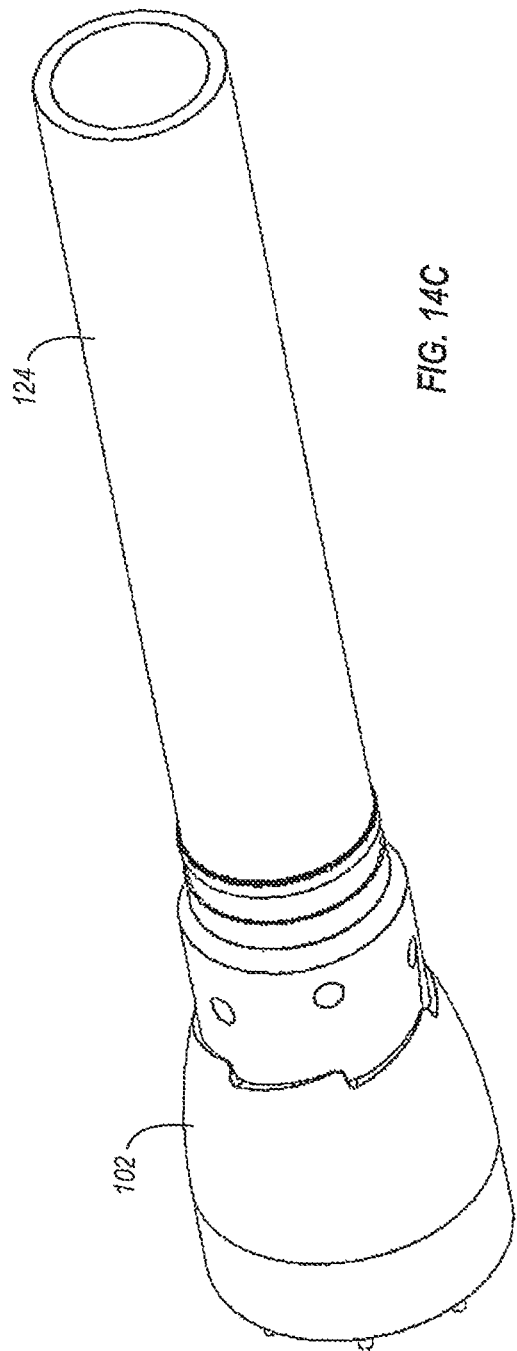

FIGS. 14A-14C are side and isometric views depicting a shoe 102 of a first frac plug 100 and the mandrel 124 of a second frac plug 100. For clarity, the other components of the first and second frac plugs 100 are not shown. As shown, the lower clutching mechanism 132 and clutching mechanism 133 are engaged. Due to the configuration of the protrusions 134 and valleys 136 of the lower clutching mechanism 132 and clutching mechanism 133, the lower frac plug 100 will tend to prevent the upper frac plug 100 from rotating when the lower frac plug 100 is being drilled.

Typically, frac plugs 100 are single use items. Instead of un-setting and removing a frac plug 100, users typically drill out a frac plug 100 with a drill, destroying the frac plug 100. Debris of destroyed frac plugs 100 can be removed from the well bore as fluids are removed. When a frac plug 100 is set, a drill can drill through it, since the plug will not rotate in the well bore casing. However, when the drill has drilled part way through a frac plug 100, the frac plug 100 may work loose from the well bore casing and may rotate with the drill, thus preventing the remainder of the frac plug 100 from being destroyed. As the drill is pushed further down the well bore, the shoe 102 of the partially destroyed frac plug 100 will eventually engage the mandrel 124 of a lower set frac plug 100. At that point, the lower clutching mechanism 132 and clutching mechanism 133 will engage each other, and the lower set frac plug 100 will stop the upper partially destroyed frac plug 100 from rotating. The drill will then continue drilling through the rest of the upper frac plug 100, thus destroying the entire frac plug 100. This process repeats from frac plug 100 to frac plug 100.

Figure 15:
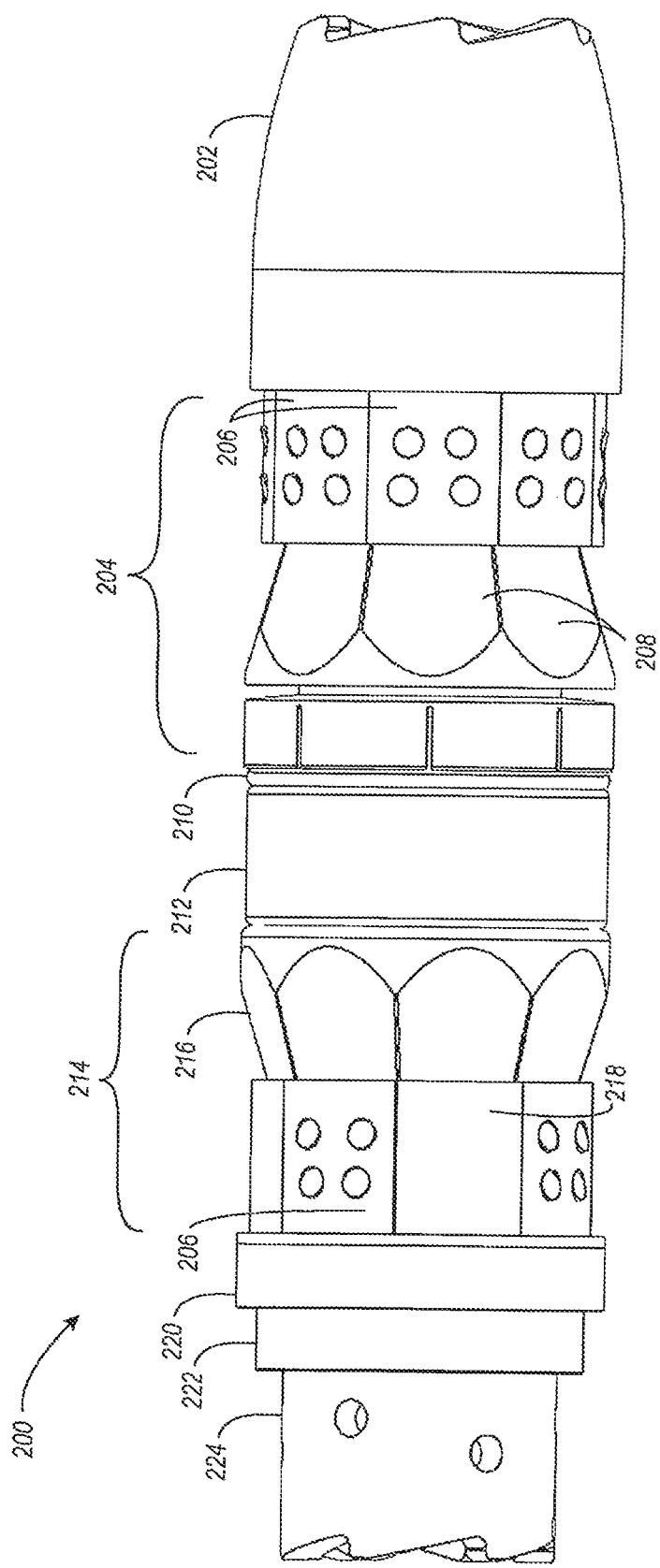
FIG. 15 is side view of another embodiment of a frac plug assembly.

FIG. 15 is a side view depicting another embodiment of a frac plug 200. The frac plug 200 is similar to the frac plug 100 shown in FIGS. 1A-1C, with a few differences. For example, the configurations of the upper and lower anchor slip assemblies 214 204 differ from the upper and lower anchor slip assemblies 114 and 104, as is described in detail below.

As with the frac plug 100, the lower end of frac plug 200 has a shoe 202. The shoe 202 has the same function as the shoe 102, described above. Above the shoe 202 is a lower anchor slip assembly 204. The lower anchor slip assembly 204 further comprises anchor slips 206 and lower wedge 208. The lower anchor slip assembly 204 is described in more detail below with respect to FIGS. 16A-16C. The anchor slips 206 are described in more detail below with respect to FIGS. 17A-17E. The lower wedge 208 are described in more detail below with respect to FIGS. 19A-19C.

Above the lower anchor slip assembly 204 is a lower element 210. The lower element 210 has the same function as the lower element 110, described above. Above the lower element 210 is upper element 212. The upper element 212 has the same function as the upper element 112, described above. Above the upper element 212 is upper anchor slip assembly 214. The upper anchor slip assembly 214 is described in more detail below with respect to FIGS. 20A-20C. The upper slip assembly 214 further comprises anchor slips 206, anchor slips 218, and upper wedge 216. The anchor slips 206 and 218 are described in more detail below with respect to FIGS. 17A-17E and 18A-18B. The upper wedge 216 are described in more detail below with respect to FIGS. 21A-21C.

Above the upper anchor slip assembly 214 is load ring 220 and load ring wedge 222. The load ring 220 and load ring wedge 222 have the same function as the load ring 120 and load ring wedge 122, described above. FIG. 15 also shows tubular mandrel 224, which extends along most of the length of the frac plug 200. The mandrel 224 has the same function as the mandrel 124, described above.

Figure 19B:
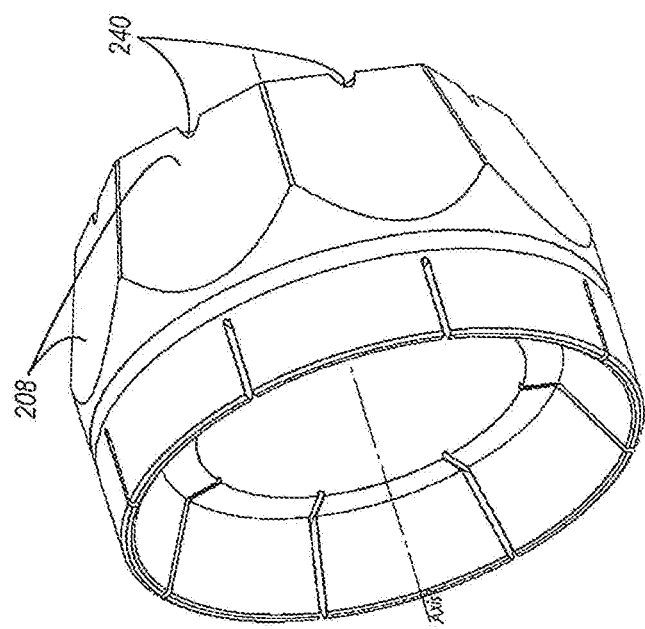
FIGS. 19A-19C are side and isometric views of the lower wedge shown in FIG. 15.
Figure 19C:
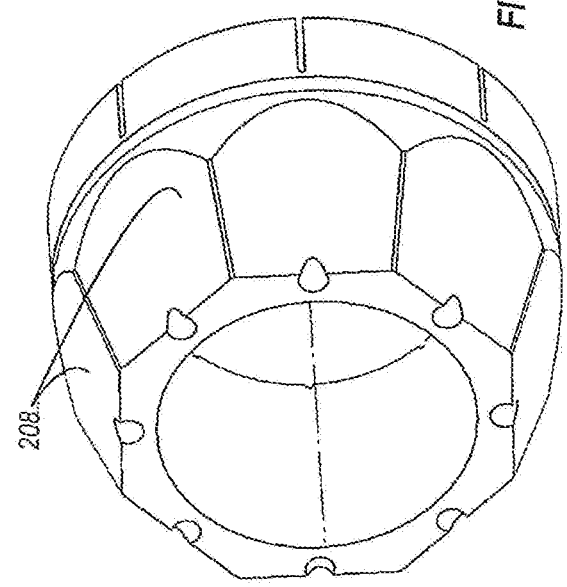
Figure 19A:
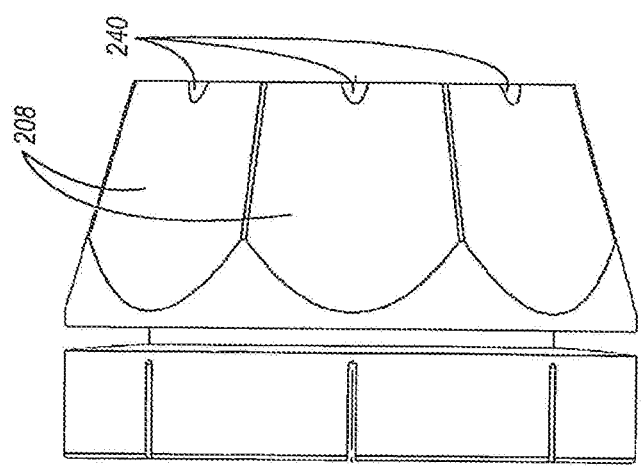
Figure 23:
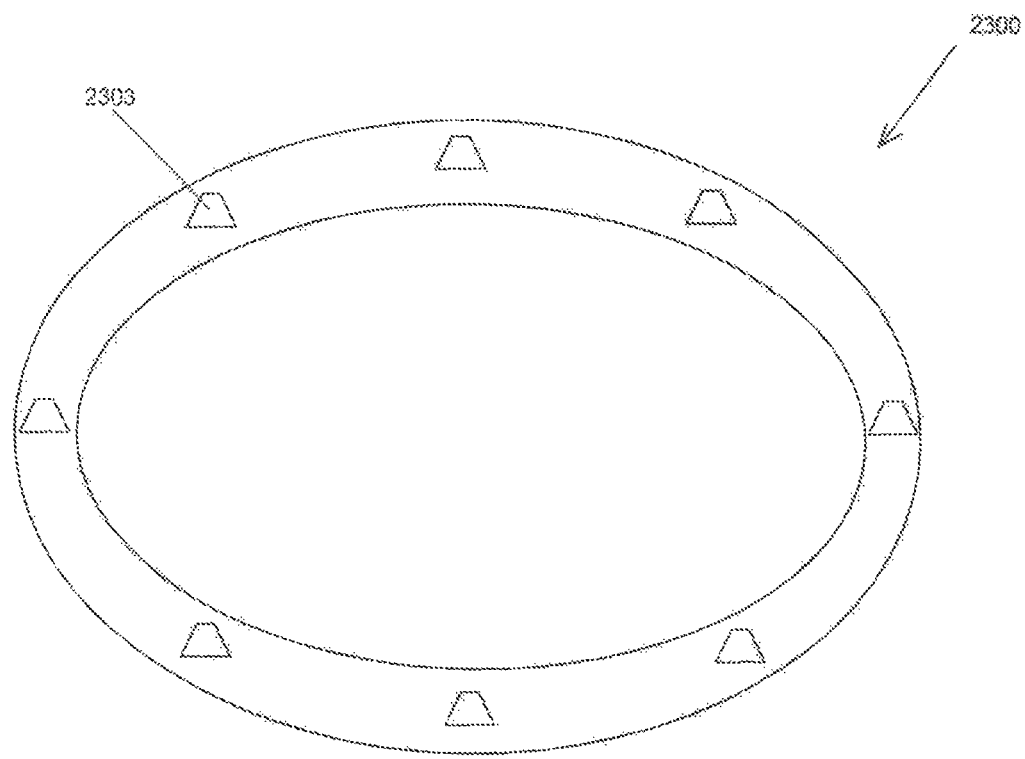
FIG. 23 is a perspective view of an anchor plate in of plug configurations.

FIGS. 16A-16C are side and isometric views of the lower anchor slip assembly 204 shown in FIG. 15. The lower anchor slip assembly 204 includes eight anchor slips 206 which each engage a corresponding lower wedge 208. As will be understood, each slip may be individually retained and move independently of other anchor. In some embodiments, a band may be used to retain each of the anchor slips 206. In other embodiments. As illustrated in FIG. 23, an anchor plate 2300, is illustrated for contact with each anchor slip. In this embodiment, a projection 2303 is provided to interface with each anchor slip 206. An anchor plate 2300 may be positioned next to each slip for both the upper slip assembly and the lower anchor slip assembly 204. In some embodiments, each slip may be individually calibrated, through interface with the anchor plate 2300 for the amount of force capable for retention. The anchors of each of the slips, may also be calibrated. To this end, the calibration may entail allowing the anchors to move at a specified force, as a non-limiting embodiment. In embodiments, the projections may be altered such that each anchor slip 206 is guided along an axis defined by the projection, thus preventing premature setting and interference with other anchor slips. As shown best in FIGS. 17A-17E, each anchor slip 206 has one anchor 238 extending toward the corresponding lower wedge 208. FIGS. 19A-19C are side and isometric views of the lower wedge 208 shown in FIG. 15. Each lower wedge 208 has one groove 240 that is each configured to receive an anchor 238 of a corresponding anchor slip 206. The combination of anchors 238 and grooves 240 help keep the anchor slips 206 aligned as they move relative to the wedge 208 when a frac plug 200 is set (described below with respect to FIGS. 22A-22B). Each anchor slip 206 includes one or more metal ceramic composite (MCC) buttons 243 that extend outward from the anchor slip 206. In the example shown in FIG. 17, each anchor slip 206 has four buttons 243. Other examples are also possible, as one skilled in the art would understand. FIG. 17D shows the anchor slip 206 without buttons 243. As shown, for each button 243, a corresponding hole 244 is formed to receive a button 243. When a frac plug 200 is set (described below), the buttons 243 engage the inner surface of the well bore casing or pipe, locking the frac plug 200 in place.

FIGS. 20A-20C are side and isometric views of the upper anchor slip assembly 214 shown in FIG. 15. The upper anchor slip assembly 214 is similar to the lower anchor slip assembly 204. The upper anchor slip assembly 214 includes eight anchor slips 206. In this example, four of the anchor slips 206 are the same as those on the lower anchor slip assembly 204. The other four anchor slips are blank anchor slips 218 that do not have MCC buttons 243. FIGS. 18A-18B are isometric views of a blank anchor slip 218. The number of buttons 243 used can be selected by a designer based on various factors, as mentioned above. In these embodiments, any number of buttons 243 may be used in combination. The number of buttons 243 may vary from each anchor slip assembly, as well as each individual slip. In other embodiments, the overall size of the anchor slips 206 may be varied, such that more or less anchor slips 206 are provided, therefore allowing different size slips and different number of anchor slips 206 used for securing performance.

Figure 21C:
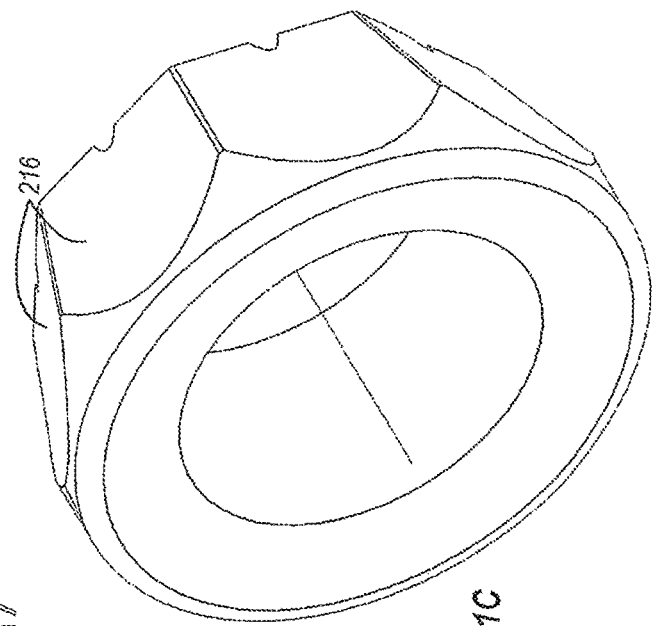
FIGS. 21A-21C are side and isometric views of the upper wedge shown in FIG. 15.
Figure 21B:
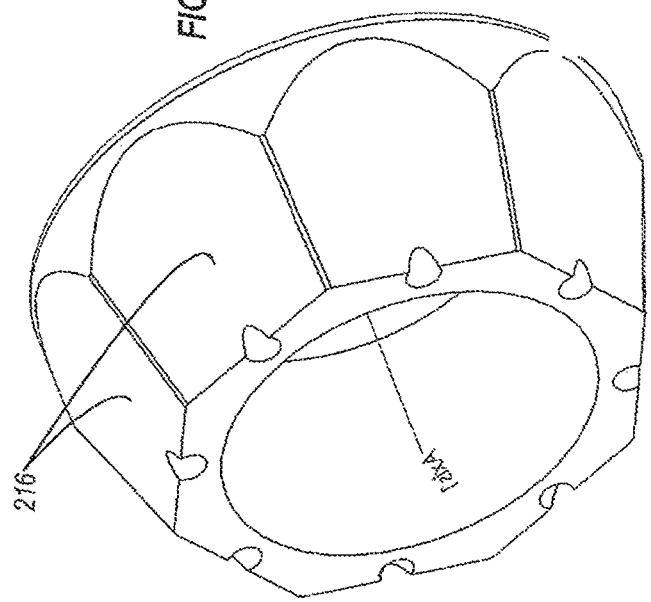
Figure 21A:
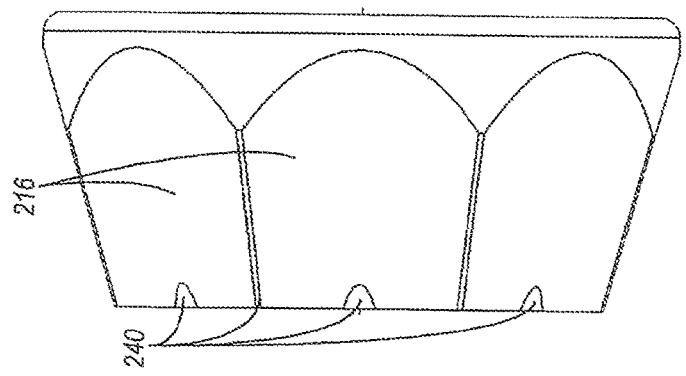

As shown in FIGS. 17A-17E and 18A-18B, each anchor slip 206 and 218 has one anchor 238 extending toward the corresponding upper wedge 216. FIGS. 21A-21C are side and isometric views of the upper wedge 216 shown in FIG. 15. Each upper wedge 216 has one groove 240 that is configured to receive an anchor 238 of a corresponding anchor slip 206 or 218. The combination of anchors 238 and grooves 240 help keep the anchor slips 206 and 218 aligned as they move relative to the wedge 216 when a frac plug 200 is set (described below with respect to FIGS. 22A-22B).

As mentioned above, during use, a frac plug can be set in place using a conventional setting tool. Generally the setting tool will engage the load ring and load causing the anchor slips to slide up the wedge, forcing the MCC buttons to press against the inner surface of the wellbore casing. FIGS. 22A-22B are side views of the frac plug 200 shown in FIG. 15 inside a well bore casing 230. For clarity, the well bore casing 230 is depicted in partial cross-sectional views. FIG. 22A shows a frac plug 200 prior to being set. As shown, the anchor slips 206 and 218 are in the un-set position, so the buttons 243 do not engage the inner surface of the well bore casing 230.

When a user wants to set the frac plug 200, a setting, tool is used. The setting tool enables users to push the components of the frac plug 200 together so the anchor slips 206 and 218 will travel up the wedge 208 and 216. When the anchor slips 206 and 218 travel far enough up the wedge 208 and 216, the buttons 243 will engage the inner surface of the casing 230, locking the frac plug 200 in place. FIG. 22B shows the frac plug 200 in the set position. As shown, the anchor slips 206 and 218 have traveled up the wedges 208 and 216, and the buttons 243 are pressed against the casing 230. Since the two sets of eight anchor slips 206 and 218 are evenly distributed radially around the frac plug 200, the frac plug 200 will self-center when set, since each anchor slip travels up its respective wedge by the same amount.

At this point, fluid can still flow through the passageway of the mandrel 224. To block the flow of fluids, a frac ball can be seated against the seat 150 of the mandrel (described above).

Figure 24:
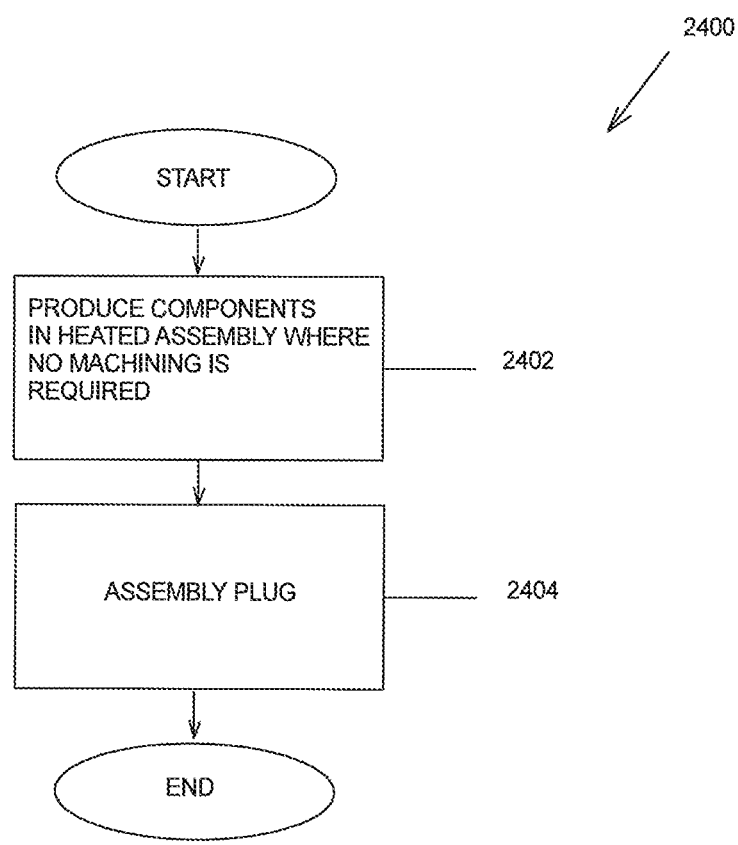
FIG. 24 is a method of manufacturing a plug in one example embodiment of the disclosure.

Referring to FIG. 24, a method 2400 for producing a plug is illustrated. In the illustrated embodiment, the method comprises, at 2402 producing each of a shoe, a lower anchor slip assembly, a lower element, an upper element, an upper anchor slip assembly with individually positionable anchors, a load ring and a tubular mandrel, wherein each of the shoe, the lower anchor slip assembly with individually postionable anchors, the lower element, the upper element, the upper anchor slip assembly, the load ring and the tubular mandrel are configured in a heated assembly arrangement and wherein no machining is required. At 2404, the method may also comprise assembling the plug wherein the plug has the lower anchor slip assembly having a first end and a second end, the lower anchor slip assembly connected at the first end to the shoe, a lower element connected to the second end of the lower anchor slip assembly, an upper element connected to the lower element, an upper anchor slip assembly having an upper anchor slip assembly first end and an upper anchor slip assembly second end, the upper anchor slip assembly connected to the upper element first end, the upper anchor slip assembly having a number of independent anchors to expand from a first diameter size to a second diameter size. The method may also provide for the load ring connected to the upper anchor slip assembly second end, the load ring wedge connected to the load ring and the tubular mandrel placed at least partially within the shoe, the lower anchor slip assembly, the lower element, the upper element, the upper anchor slip assembly, the load ring and the load ring wedge, wherein linear movement of the tubular mandrel causes movement of the upper anchor slip assembly to expand a set of upper anchor slips in a radial direction and linear movement of the tubular mandrel is further configured to expand a set of lower anchor slips in a radial direction.

In one example embodiment, a plug is described. The plug may comprise a shoe, a lower anchor slip assembly having a first end and a second end, the lower anchor slip assembly connected at the first end to the shoe, the lower anchor slip assembly having a number of independent anchors to expand from a first diameter size to a second diameter size, a lower element connected to the second end of the lower anchor slip assembly, and an upper element connected to the lower element. The plug may also comprise an upper anchor slip assembly having an upper anchor slip assembly first end and an upper anchor slop assembly second end, the upper anchor slip assembly connected to the upper element first end; a load ring connected to the upper anchor slip assembly second end, and a load ring wedge connected to the load ring, the upper anchor slip assembly having a number of independent anchors to expand from a first diameter size to a second diameter size wherein each of the independent anchors are calibrated. The plug may also comprise a tubular mandrel placed at least partially within the shoe, the lower anchor slip assembly, the lower element, the upper element, the upper anchor slip assembly, the load ring and the load ring wedge, wherein linear movement of the tubular mandrel causes movement of the upper anchor slip assembly to expand a set of upper anchor slips in a radial direction and linear movement of the tubular mandrel is further configured to expand a set of lower anchor slips in a radial direction.

In another example embodiment, the plug may be configured wherein the lower anchor slip assembly is configured with a lower wedge upon which the lower anchor slips expand around.

In another example embodiment, the plug may be configured wherein the upper anchor slip assembly is configured with an upper wedge upon which the upper anchor slips expand around.

In another example embodiment, the plug may be configured wherein the shoe is configured with a lower clutch mechanism.

In another example embodiment, the plug may be configured wherein the lower clutch mechanism is configured with a surface with protrusions and valleys.

In another example embodiment, the plug may be configured wherein the tubular mandrel is configured with a clutching mechanism to interface with a lower clutch mechanism of a shoe of a different plug.

In another example embodiment, the plug may be configured wherein the tubular mandrel is configured with a plurality of holes for attaching of a setting tool.

In another example embodiment, the plug may be configured wherein the mandrel is configured with a seat configured to interface with a ball to stop a flow of fluid through the mandrel when the mandrel is in a downhole environment.

In another example embodiment, a plug is described. The plug may comprise a shoe configured with a lower clutch mechanism, a lower anchor slip assembly having a first end and a second end, the lower anchor slip assembly positioned at the first end to the shoe, the lower anchor slip assembly having a number of independent anchors to expand from the first diameter size to the second diameter size the lower slip assembly configured to expand from a first diameter size to a second diameter size, and a lower element positioned next to the second end of the lower anchor slip assembly. The plug may further comprise an upper element connected to the lower element, and an upper anchor slip assembly having an upper anchor slip assembly first end and a upper anchor slip assembly second end, the upper anchor slip assembly positioned next to the upper element first end, the upper anchor slip assembly configured to expand from a first upper anchor slip assembly diameter size to a second upper anchor slip assembly diameter size the upper anchor slip assembly having a number of independent upper anchors to expand from the first upper anchor slip assembly diameter size to the second upper anchor slip assembly diameter size. The plug may further comprise a load ring positioned next to the upper anchor slip assembly second end; a load ring wedge connected to the load ring, and a tubular mandrel placed at least partially within the shoe, the lower anchor slip assembly, the lower element, the upper element, the upper anchor slip assembly, the load ring and the load ring wedge, wherein linear motion of the tubular mandrel causes movement of the upper anchor slip assembly to expand a set of upper anchor slips in a radial direction and linear motion of the tubular mandrel is further configured to expand a set of lower anchor slips in a radial direction.

In another example embodiment, the plug may be configured wherein the upper anchor slip assembly is configured with an upper wedge.

In another example embodiment, the plug may be configured wherein the upper anchor slip assembly is configured with upper anchor slips configured to interact with the upper wedge.

In another example embodiment, the plug may be configured wherein the lower anchor slip assembly is configured with a lower wedge.

In another example embodiment, the plug may be configured wherein the lower anchor slip assembly is configured with lower anchor slips configured to interact with the lower wedge.

In another example embodiment, the plug may be configured wherein each of the lower anchor slips is configured with buttons to interact with an interior diameter of a pipe.

In another example embodiment, the plug may be configured wherein the upper anchor slips are configured with buttons to interact with an interior diameter of a pipe.

In another example embodiment, the mandrel is configured with a clutching mechanism.

In another example embodiment, the plug may be configured such that the clutching mechanism of the mandrel is configured to interact with the lower clutch mechanism of another shoe.

In another example embodiment, a method of making a plug is disclosed. The method may comprise producing each of a shoe, a lower anchor slip assembly, a lower element, an upper element, an upper anchor slip assembly with individually positionable anchors, a load ring and a tubular mandrel, wherein each of the shoe, the lower anchor slip assembly with individually postionable anchors, the lower element, the upper element, the upper anchor slip assembly, the load ring and the tubular mandrel are configured in a heated assembly arrangement and wherein no machining on an inside diameter of the mandrel is required. The method may also comprise assembling the plug wherein the plug has the lower anchor slip assembly having a first end and a second end, the lower anchor slip assembly connected at the first end to the shoe, a lower element connected to the second end of the lower anchor slip assembly, an upper element connected to the lower element, an upper anchor slip assembly having an upper anchor slip assembly first end and an upper anchor slip assembly second end, the upper anchor slip assembly connected to the upper element first end, the upper anchor slip assembly having a number of independent anchors to expand from a first diameter size to a second diameter size. The method may also be performed wherein the load ring connected to the upper anchor slip assembly second end; the load ring wedge connected to the load ring; and the tubular mandrel placed at least partially within the shoe, the lower anchor slip assembly, the lower element, the upper element, the upper anchor slip assembly, the load ring and the load ring wedge, wherein linear movement of the tubular mandrel causes movement of the upper anchor slip assembly to expand a set of upper anchor slips in a radial direction and linear movement of the tubular mandrel is further configured to expand a set of lower anchor slips in a radial direction.

In another example embodiment, the method may be performed wherein at least one inner diameter of the show, the lower anchor slip assembly, the lower element, the upper element, the upper anchor slip assembly, the load ring and the tubular mandrel have a shaped internal diameter.

In another example embodiment, the method may be performed wherein a glass material used to construct at least one of the shoe, the lower anchor slip assembly, the lower element, the upper element, the upper anchor slip assembly, the load ring and the tubular mandrel has at least two diameters.

In another example embodiment, the plug may be made of materials that may be drilled.

In the preceding detailed description, the disclosure is described with reference to specific exemplary embodiments thereof. Various modifications and changes may be made thereto without departing from the broader spirit and scope of the disclosure as set forth in the claims. The specification and drawings are, accordingly, to be regarded in an illustrative rather than a restrictive sense.

What is claimed is:

1. A plug, comprising:
   a shoe;
   a lower anchor slip assembly having a first end and a second end, the lower anchor slip assembly connected at the first end to the shoe, the lower anchor slip assembly having a lower wedge and a number of independent lower anchors slips, wherein the lower wedge includes a plurality of grooves configured to receive a corresponding plurality of anchors on the lower anchor slips,
   wherein the lower anchor slip assembly is configured to expand from a first diameter size to a second diameter size, wherein the lower anchor slips are independently calibrated to move from the first diameter size to the second diameter size upon a specified force,
   a lower element connected to the second end of the lower anchor slip assembly;
   an upper element connected to the lower element;
   an upper anchor slip assembly having an upper anchor slip assembly first end and an upper anchor slip assembly second end, the upper anchor slip assembly connected to an upper element first end, the upper anchor slip assembly having an upper wedge and a number of independent upper anchors slips, wherein the upper wedge includes a plurality of grooves configured to receive a corresponding plurality of anchors on the upper anchor slips;
   wherein the upper anchor slip assembly is configured to expand from a first diameter size to a second diameter size, wherein the upper anchor slips are independently calibrated to move from the first diameter size to the second diameter size upon a specified force;
   a load ring connected to the upper anchor slip assembly second end;
   a load ring wedge connected to the load ring; and
   a tubular mandrel placed at least partially within the shoe, the lower anchor slip assembly, the lower element, the upper element, the upper anchor slip assembly, the load ring and the load ring wedge, wherein the tubular mandrel is configured with an internal seat within the plug configured to interface with a ball to stop a flow of fluid through the mandrel when the mandrel is in a downhole environment.

2. The plug according to claim 1, wherein the lower anchor slips expand around the lower wedge.

3. The plug according to claim 1, wherein the upper anchor slips expand around the upper wedge.

4. The plug according to claim 1, wherein the shoe is configured with a lower clutch mechanism.

5. The plug according to claim 4, wherein the lower clutch mechanism is configured with a surface with protrusions and valleys to have multiple locking positions.

6. The plug according to claim 5, wherein the tubular mandrel is configured with a clutching mechanism to interface with a lower clutch mechanism of a shoe of a different plug.

7. The plug according to claim 1, wherein the tubular mandrel is configured with a plurality of holes for attaching of a setting tool.

8. A method of making a plug, comprising:

producing each of a shoe, a lower anchor slip assembly with individually positionable lower anchor slips, a lower element, an upper element, an upper anchor slip assembly with individually positionable upper anchor slips, a load ring, a load ring wedge, and a tubular mandrel, wherein each of the shoe, the lower anchor slip assembly, the lower element, the upper element, the upper anchor slip assembly, the load ring, the load ring wedge, and the tubular mandrel are configured in a heated assembly arrangement and wherein no machining is required on an inside diameter of the mandrel; and assembling the plug wherein the plug has the lower anchor slip assembly having a first end and a second end, the lower anchor slip assembly connected at the first end to the shoe, the lower element connected to the second end of the lower anchor slip assembly, the upper element connected to the lower element, the upper anchor slip assembly having an upper anchor slip assembly first end and an upper anchor slip assembly second end, the upper anchor slip assembly connected to an upper element first end, the upper anchor slip assembly having a number of independent anchor slips to expand from a first diameter size to a second diameter size;

the load ring connected to the upper anchor slip assembly second end;

the load ring wedge connected to the load ring; and the tubular mandrel placed at least partially within the shoe, the lower anchor slip assembly, the lower element, the upper element, the upper anchor slip assembly, the load ring and the load ring wedge, wherein linear movement of the tubular mandrel causes movement of the upper anchor slip assembly to expand a set of upper anchor slips in a radial direction and linear movement of the tubular mandrel is further configured to expand a set of lower anchor slips in a radial direction, wherein the mandrel is configured with a seat configured to interface with a ball to stop a flow of fluid through the mandrel when the mandrel is in a downhole environment, wherein the lower anchor slip assembly includes a lower wedge having a plurality of grooves configured to receive a corresponding plurality of anchors on the lower anchor slips and wherein the upper anchor slip assembly includes an upper wedge having a plurality of grooves configured to recieve a corresponding plurality of anchors on the upper achor slips.

9. The method according to claim 8, wherein at least one inner diameter of the shoe, the lower anchor slip assembly, the lower element, the upper element, the upper anchor slip assembly, the load ring and the tubular mandrel have a shaped internal diameter.

10. The method according to claim 8, wherein a glass material used to construct at least one of the shoe, the lower anchor slip assembly, the lower element, the upper element, the upper anchor slip assembly, the load ring and the tubular mandrel has at least two diameters.

* * * * *